US012249419B2

(12) United States Patent
Blair et al.

(10) Patent No.: US 12,249,419 B2
(45) Date of Patent: Mar. 11, 2025

(54) METHODS AND SYSTEMS FOR AUTOMATED CLINICAL WORKFLOWS

(71) Applicant: Eko Health, Inc., Emeryville, CA (US)

(72) Inventors: Richard N. Blair, Kent, WA (US); John Prince, New York, NY (US); John Maidens, Berkeley, CA (US); Niladri Bora, Grass Valley, CA (US); Tyler Crouch, San Francisco, CA (US); Jordan Crivelli-Decker, El Cerrito, CA (US); Subramaniam Venkatraman, Lafayette, CA (US); John Zorko, Vallejo, CA (US); Neraj Bobra, San Jose, CA (US)

(73) Assignee: EKO HEALTH, INC., Emeryville, CA (US)

( * ) Notice: Subject to any disclaimer, the term of this patent is extended or adjusted under 35 U.S.C. 154(b) by 793 days.

(21) Appl. No.: 17/449,436

(22) Filed: Sep. 29, 2021

(65) Prior Publication Data

US 2023/0096006 A1 Mar. 30, 2023

(51) Int. Cl.
*G16H 40/63* (2018.01)
*A61B 7/04* (2006.01)
(Continued)

(52) U.S. Cl.
CPC ............... *G16H 40/63* (2018.01); *A61B 7/04* (2013.01); *G06F 3/14* (2013.01); *G06T 11/00* (2013.01);
(Continued)

(58) Field of Classification Search
CPC .......... G16H 40/63; A61B 7/04; A61B 7/003; A61B 5/684; A61B 5/7221; A61B 5/0006;
(Continued)

(56) References Cited

U.S. PATENT DOCUMENTS

2011/0208009 A1* 8/2011 Fu .......................... A61B 5/024 600/300
2016/0354054 A1 12/2016 Minegishi et al.
2019/0279768 A1* 9/2019 Bates ..................... G16H 50/20
(Continued)

FOREIGN PATENT DOCUMENTS

CN 110897654 A 3/2020
WO 2015117035 A1 8/2015
(Continued)

OTHER PUBLICATIONS

Great Britain Intellectual Property Office, Search Report under Section 17(5) Issued in Application No. GB2207821.6, Nov. 24, 2022, 5 pages.

(Continued)

*Primary Examiner* — Devin B Henson
*Assistant Examiner* — Jennifer Grace Baires-Tweed
(74) *Attorney, Agent, or Firm* — McCoy Russell LLP

(57) ABSTRACT

Various methods and systems are provided for an automated clinical exam workflow. In one example, method comprises performing a signal quality check of an electronic stethoscope at a first recording location on a subject, recording physiological data for an exam at the first recording location via the electronic stethoscope in response to the signal quality check satisfying a quality threshold, and outputting a signal quality alert in response to the signal quality check not satisfying the quality threshold. In this way, clinically relevant data may be obtained with reduced user effort and fewer manual inputs.

16 Claims, 12 Drawing Sheets

(51) Int. Cl.

| | |
|---|---|
| ***G06F 3/14*** | (2006.01) |
| ***G06T 11/00*** | (2006.01) |
| ***G08B 7/06*** | (2006.01) |
| ***G08B 21/18*** | (2006.01) |
| ***H04N 7/18*** | (2006.01) |
| ***H04R 1/46*** | (2006.01) |

(52) U.S. Cl.
CPC ............ *G08B 7/06* (2013.01); *G08B 21/182* (2013.01); *H04N 7/183* (2013.01); *H04R 1/46* (2013.01)

(58) Field of Classification Search
CPC ......... A61B 5/0245; A61B 5/33; A61B 5/332; G06F 3/14; G06T 11/00; G08B 7/06; G08B 21/182; G08B 21/0211; G08B 29/18; H04N 7/183; H04R 1/46; G09G 2380/08
See application file for complete search history.

(56) References Cited

U.S. PATENT DOCUMENTS

2021/0259560 A1 8/2021 Venkatraman et al.
2022/0054008 A1 2/2022 Venkatraman et al.

FOREIGN PATENT DOCUMENTS

WO 2019173412 A1 9/2019
WO 2020041363 A1 2/2020

OTHER PUBLICATIONS

Great Britain Intellectual Property Office, Search Report under Section 17(6) Issued in Application No. GB2207821.6, Nov. 24, 2022, 5 pages.
Great Britain Intellectual Property Office, Search Report under Section 17(6) Issued in Application No. GB2207821.6, Apr. 20, 2023, 2 pages.

* cited by examiner

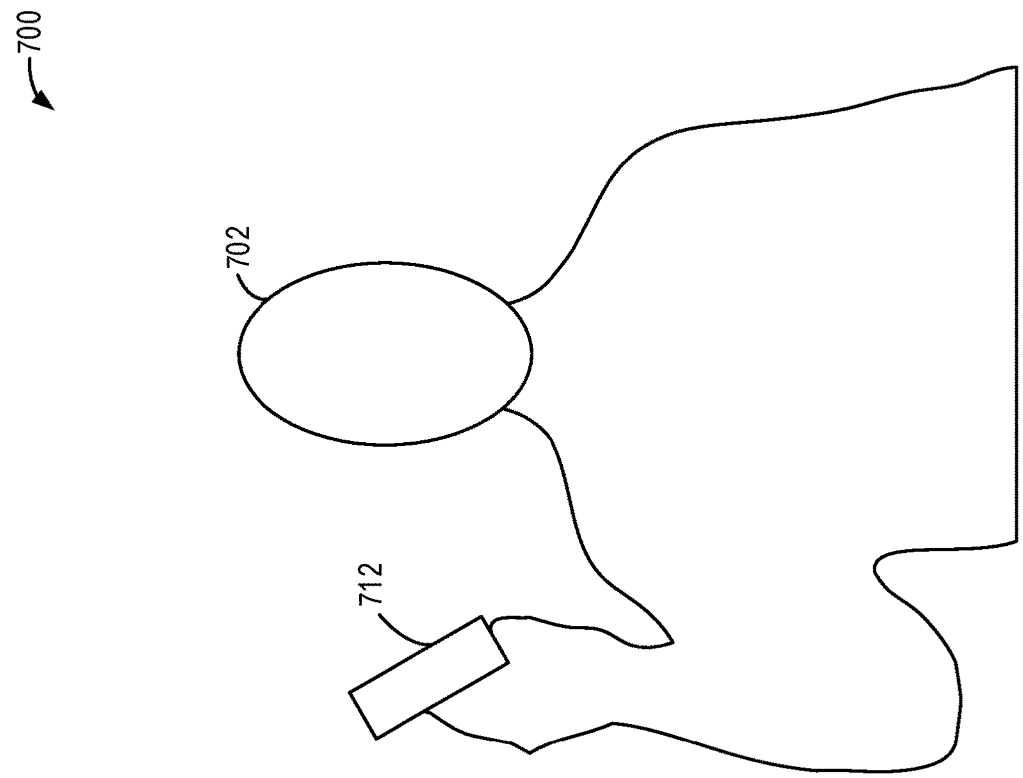
FIG. 7
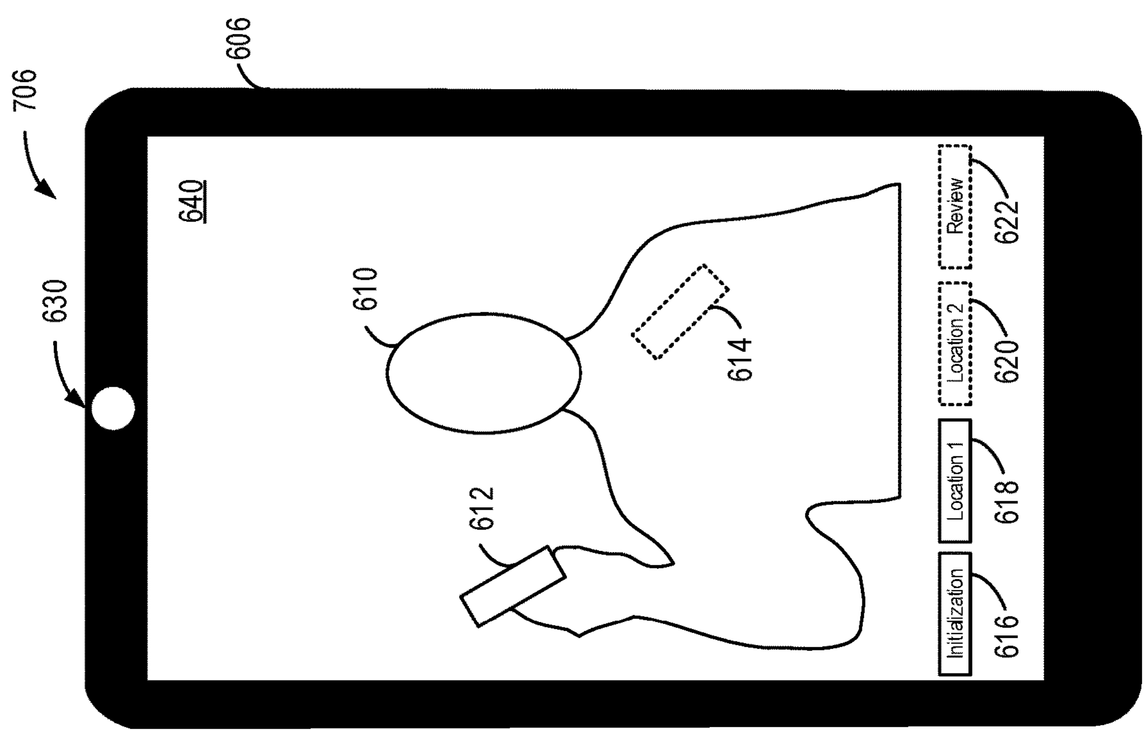

METHODS AND SYSTEMS FOR AUTOMATED CLINICAL WORKFLOWS

FIELD

The present description relates generally to medical devices utilizing wireless electronic communication and automated workflows.

BACKGROUND/SUMMARY

Remote monitoring devices have been shown to be an inexpensive and effective solution to providing patient care when in-person consultations are impossible or unfeasible. Examples of remote monitoring devices include digital stethoscopes, heart rate monitors, handheld echocardiography (HHE) or portable cardiac ultrasound devices, and other similar devices capable of recording time-varying patient data, as well as devices that capture instantaneous data such as glucose monitoring devices, blood pressure monitors, pulse oximeters, and so on. Remote monitoring may involve acquiring patient data via a monitoring device and transmitting the patient data to a remote caregiver (e.g., telemedicine).

Listening to the internal sounds of the body (e.g., heart sounds, breath sounds, and/or bowel sounds) is known as auscultation. For example, a patient may use a digital stethoscope to record a sample of their heart sounds, which are subsequently transmitted to a specialist caregiver. However, an auscultation exam takes a high degree of skill both in the placement of the remote monitoring device (e.g., the digital stethoscope, recording device, etc.) and in the interpretation of the sounds. Further, the auscultation exam may utilize recordings from multiple locations. In a cardiac exam, for example, there are four prescribed locations. To obtain an accurate diagnostic outcome, it is desired for the transmitted or recorded sounds to be of the highest quality possible for each location. As such, it may be difficult for an untrained or novice user to accurately place the remote monitoring device in each location, identify when the best signal quality is obtained in each location, and trigger the transmission or recording of the sounds accordingly. Further, even when the user is highly trained, a workflow that identifies accurate placement and/or high signal quality may decrease the auscultation exam time and decrease user effort.

As still another example, additional data, such as electrocardiogram (ECG) data, may be collected at the same time as the sound data. This further complicates the process as signal quality from all data sources may be taken into account. ECG data quality, for example, is dependent on factors such as body hair, subcutaneous tissue, skin type, etc. The overall process can be tedious, time consuming and error prone.

In one example, the issues described above may be addressed by a method, comprising: performing a signal quality check of an electronic stethoscope at a first recording location on a subject; recording physiological data for an exam at the first recording location via the electronic stethoscope in response to the signal quality check satisfying a quality threshold; and outputting a signal quality alert in response to the signal quality check not satisfying the quality threshold. In this way, clinically relevant physiological data may be obtained with reduced user effort and fewer manual inputs.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIG. 7 shows an example of a user and computer display for an asynchronous auscultation examination.

DETAILED DESCRIPTION

Figure 1A:
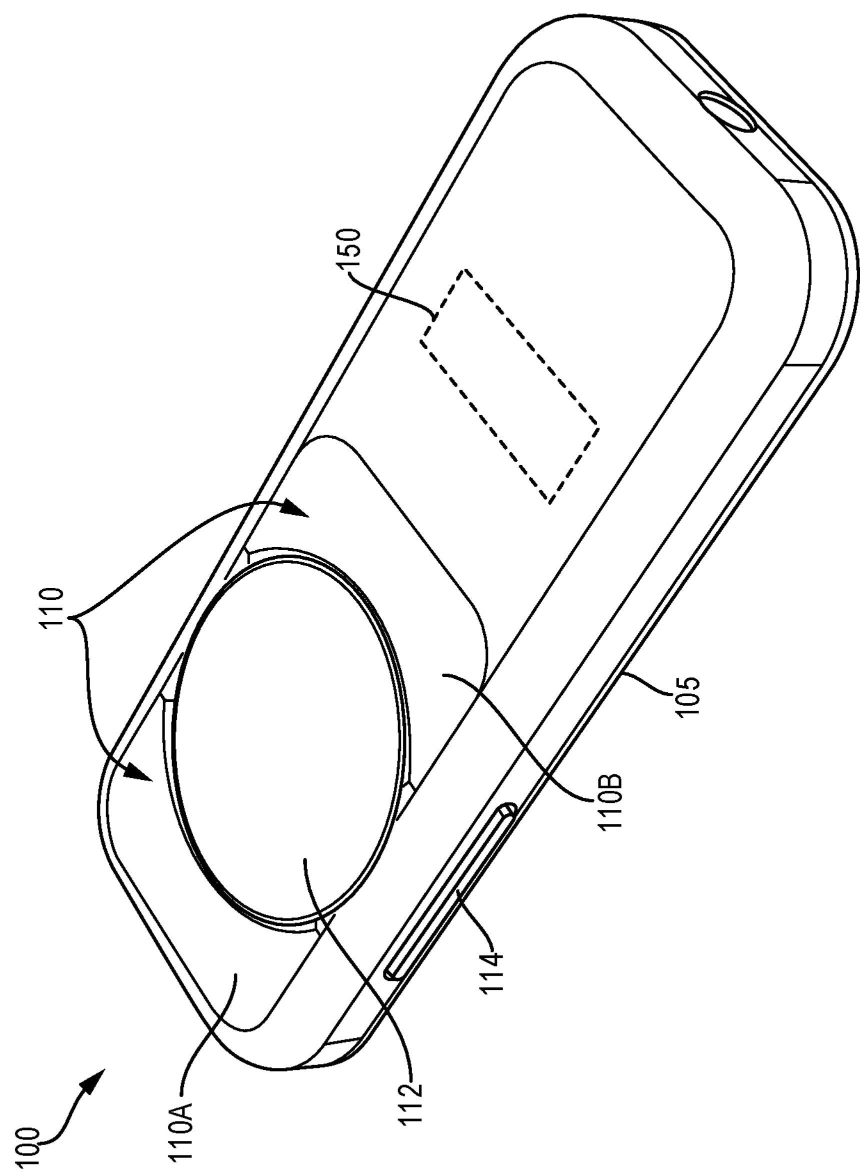
FIG. 1A shows a front perspective view of an exemplary electronic stethoscope.
Figure 1B:
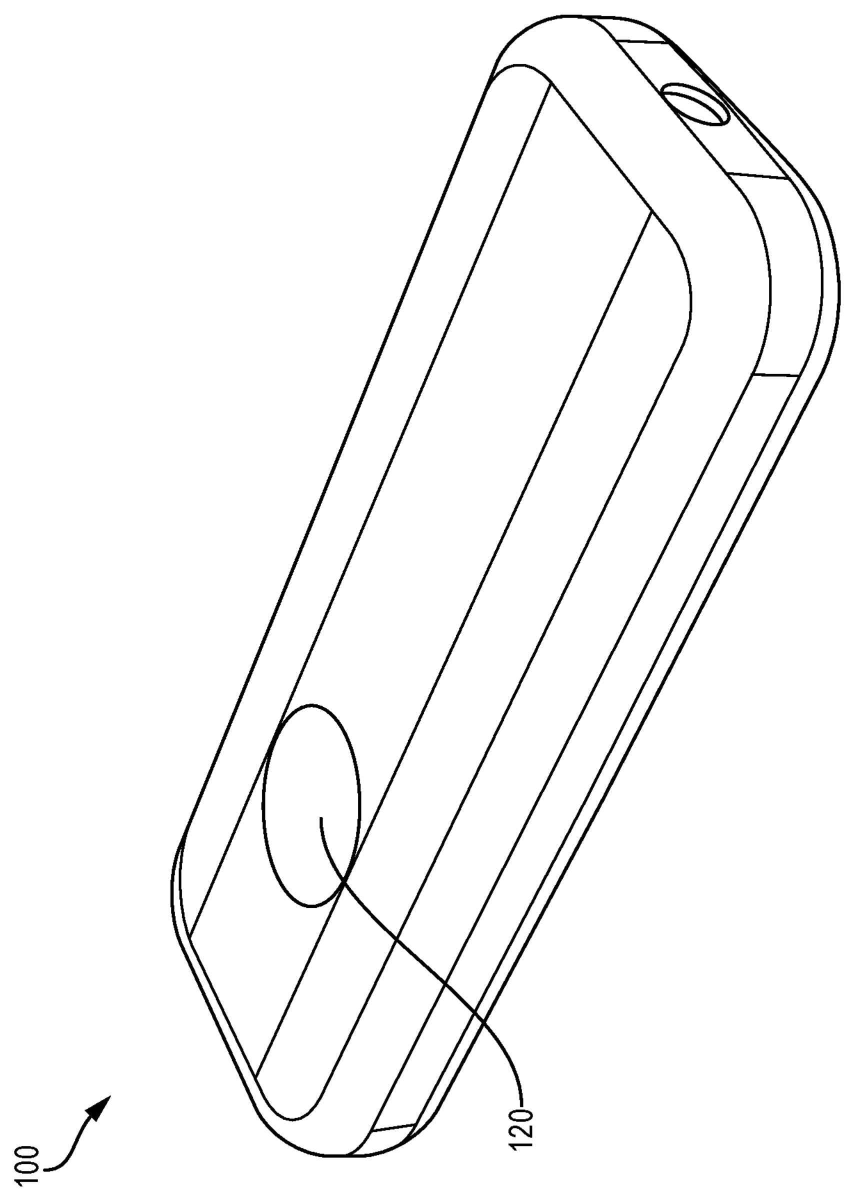
FIG. 1B shows a back perspective view of the exemplary monitoring device of FIG. 1A.
Figure 3:
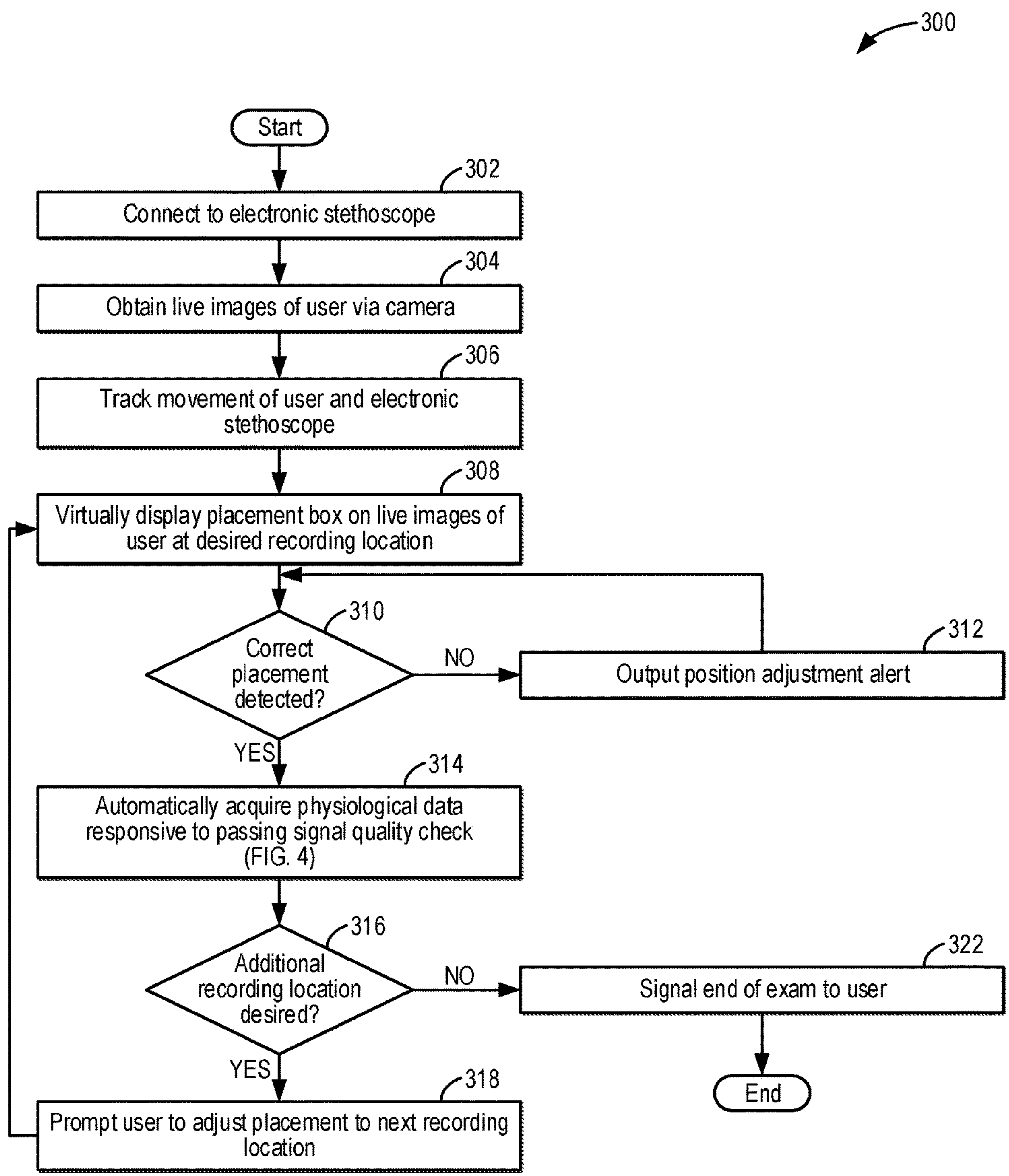
FIG. 3 shows a flowchart for a method to guide a user through medical examination.
Figure 4:
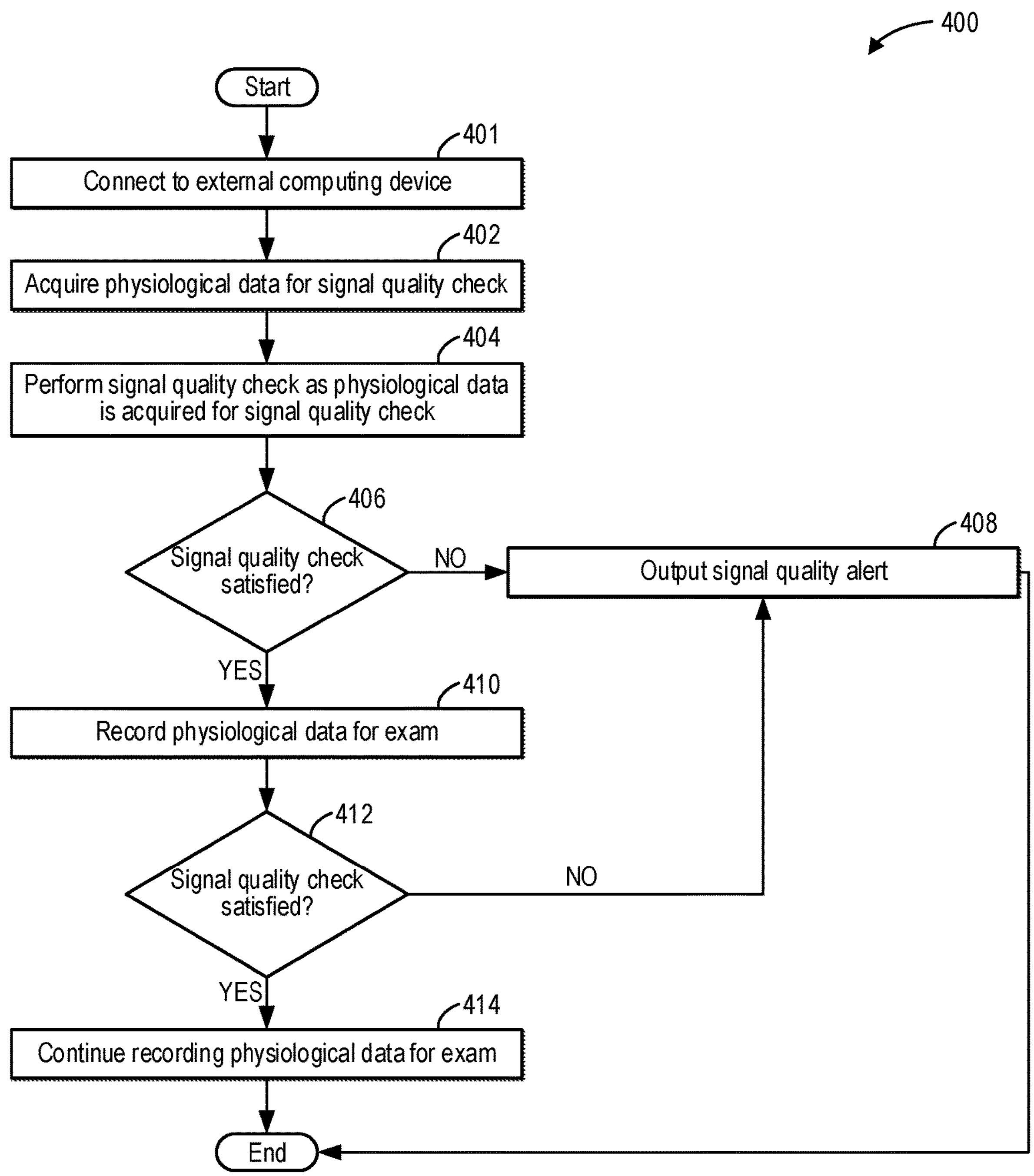
FIG. 4 shows a flowchart for a method for an electronic stethoscope performing a physiological data quality check.

The following description relates to systems and methods for a digital health monitoring device, such as the electronic stethoscope shown in FIGS. 1A and 1B. In some examples, the electronic stethoscope may contain the internal components shown in FIG. 2 and may be in communication with an external computing device, also shown in FIG. 2. The electronic stethoscope may be placed on a subject (e.g., a patient), such as on a skin of the subject, in order to measure physiological data from the subject. The physiological data may include ECG data and/or audio data, for example. In cases of remote examination, the user of the electronic stethoscope may be an untrained patient and may desire guidance on the placement of the electronic stethoscope during a medical examination. Therefore, a method for guiding the user through a medical exam using the external computing device and virtual reality technology is shown in FIG. 3. In order to confirm that the physiological data gathered by the electronic stethoscope is of a high enough quality for diagnostic usage, a method for checking the signal quality is shown in FIG. 4. The method shown in FIG. 4 may include a machine learning algorithm, such as the example algorithm shown in FIG. 5, in order to confirm the quality of the physiological data.

Figure 6:
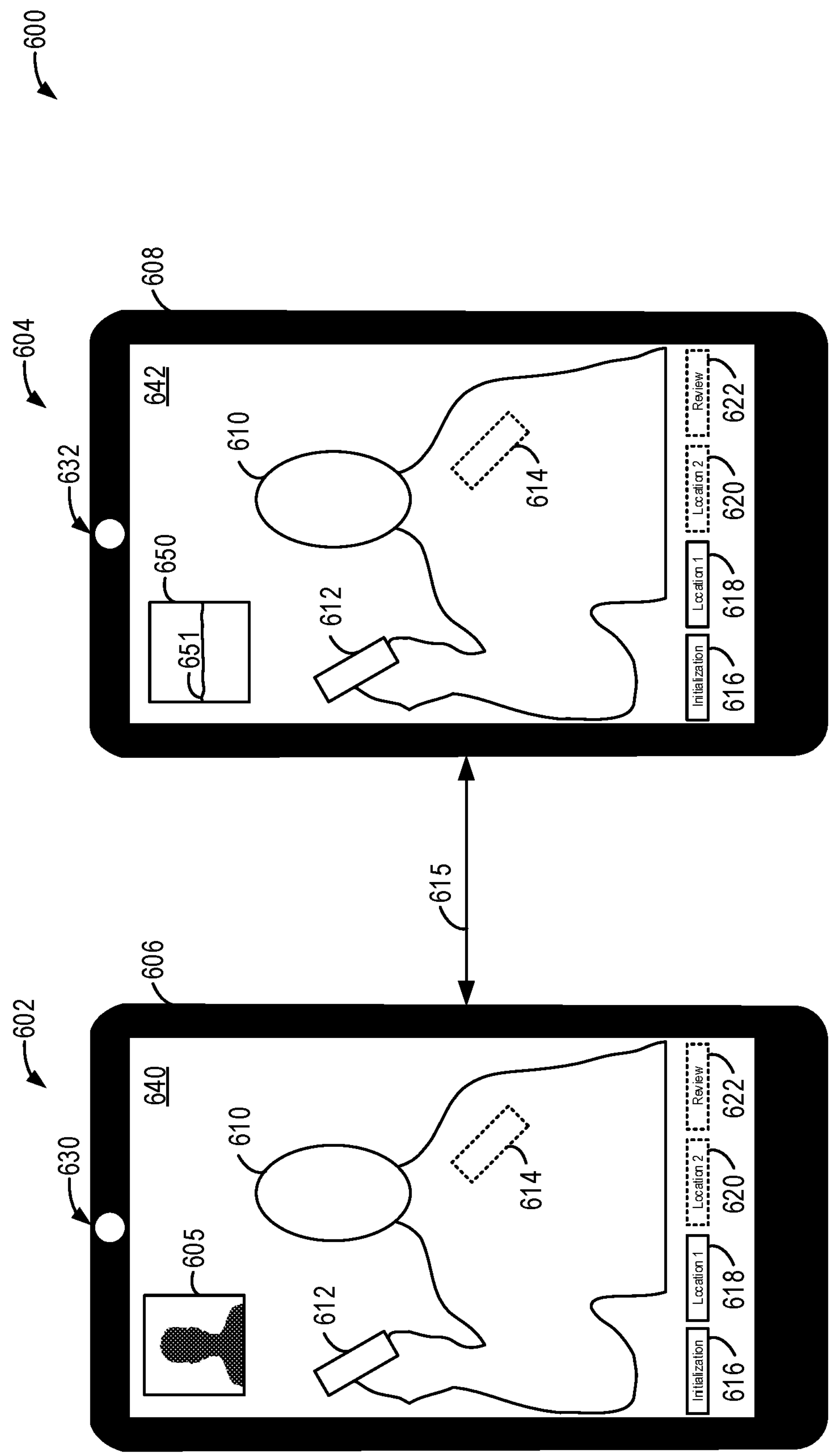
FIG. 6 shows an example of a computer display for a synchronous auscultation examination.
Figure 8B:
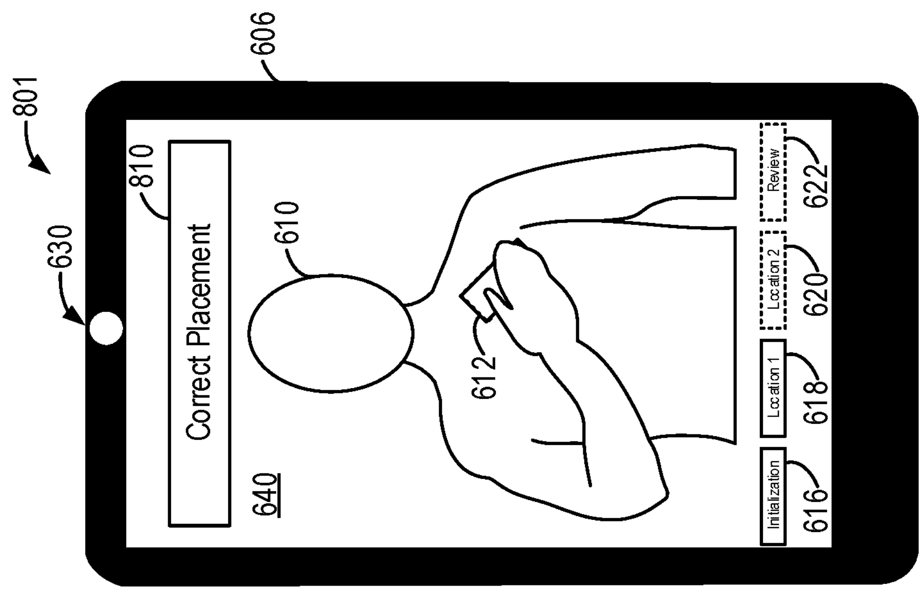
FIG. 8B shows an example of a computer display indicating a correct placement of an electronic stethoscope.
Figure 8A:
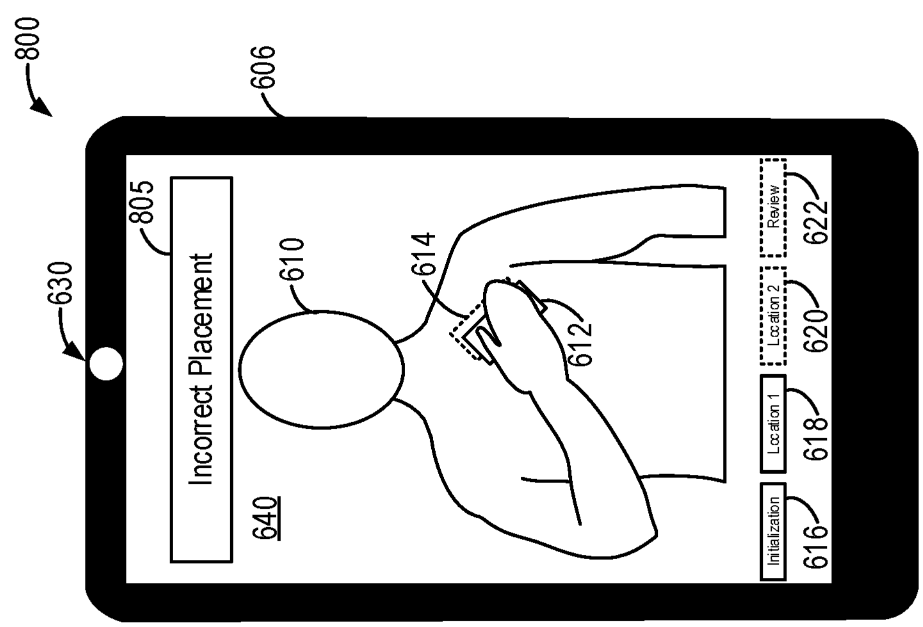
FIG. 8A shows an example of a computer display indicating an incorrect placement of an electronic stethoscope.
Figure 9:
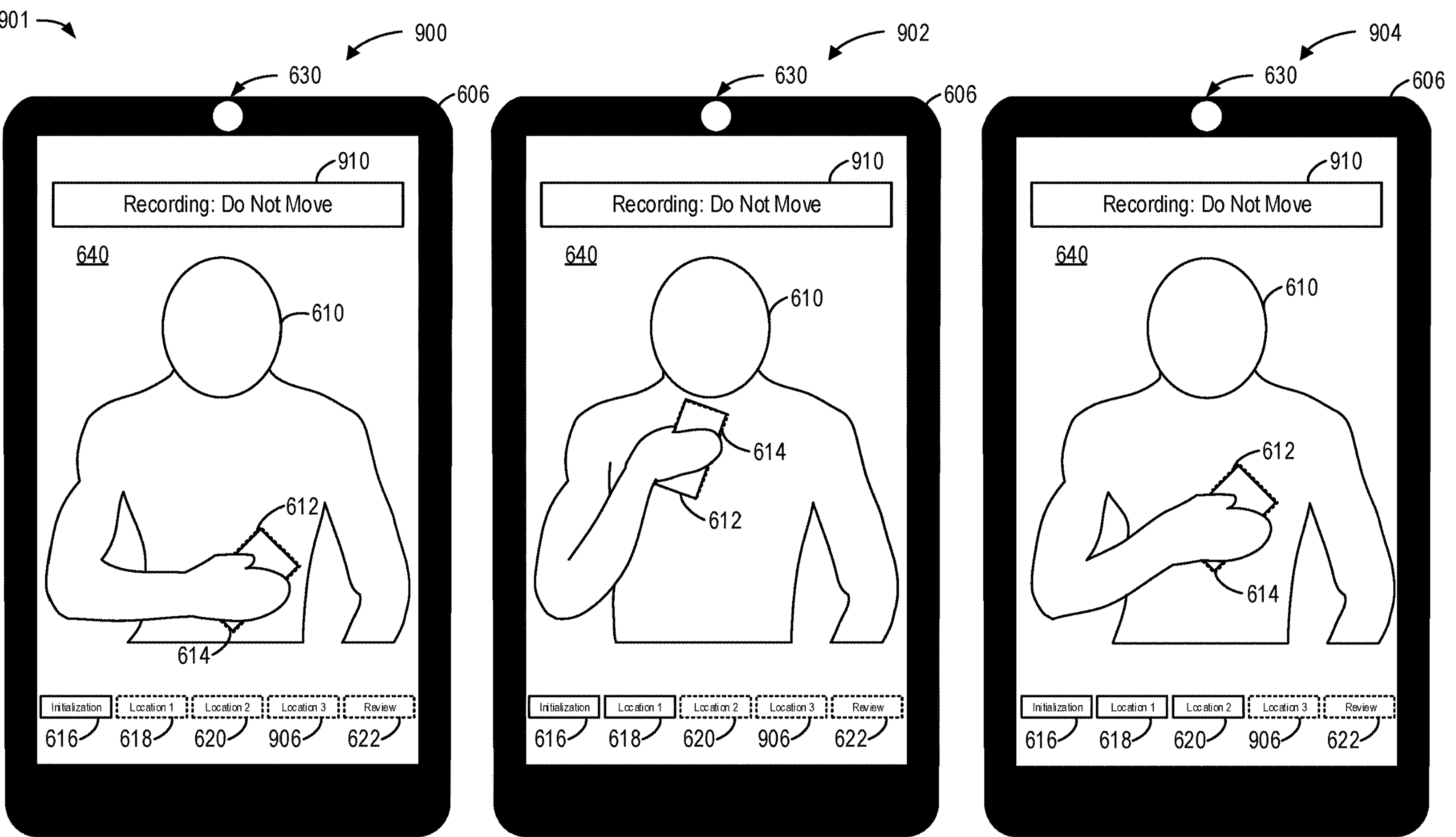
FIG. 9 shows an example of a series of computer displays during a medical examination having multiple prescribed recording locations.
Figure 10:
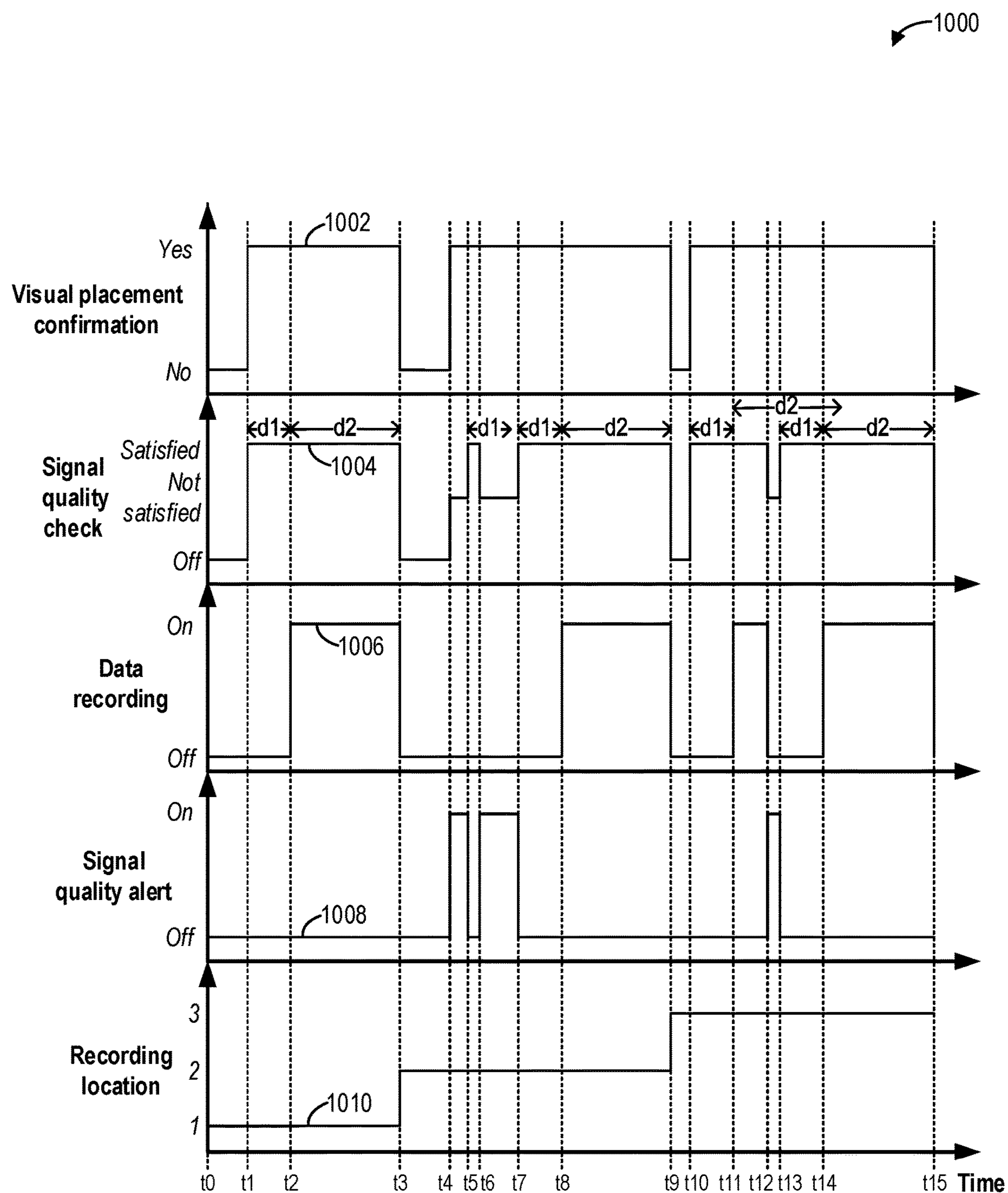
FIG. 10 shows a first example timeline of an electronic stethoscope performing a medical exam.
Figure 11:
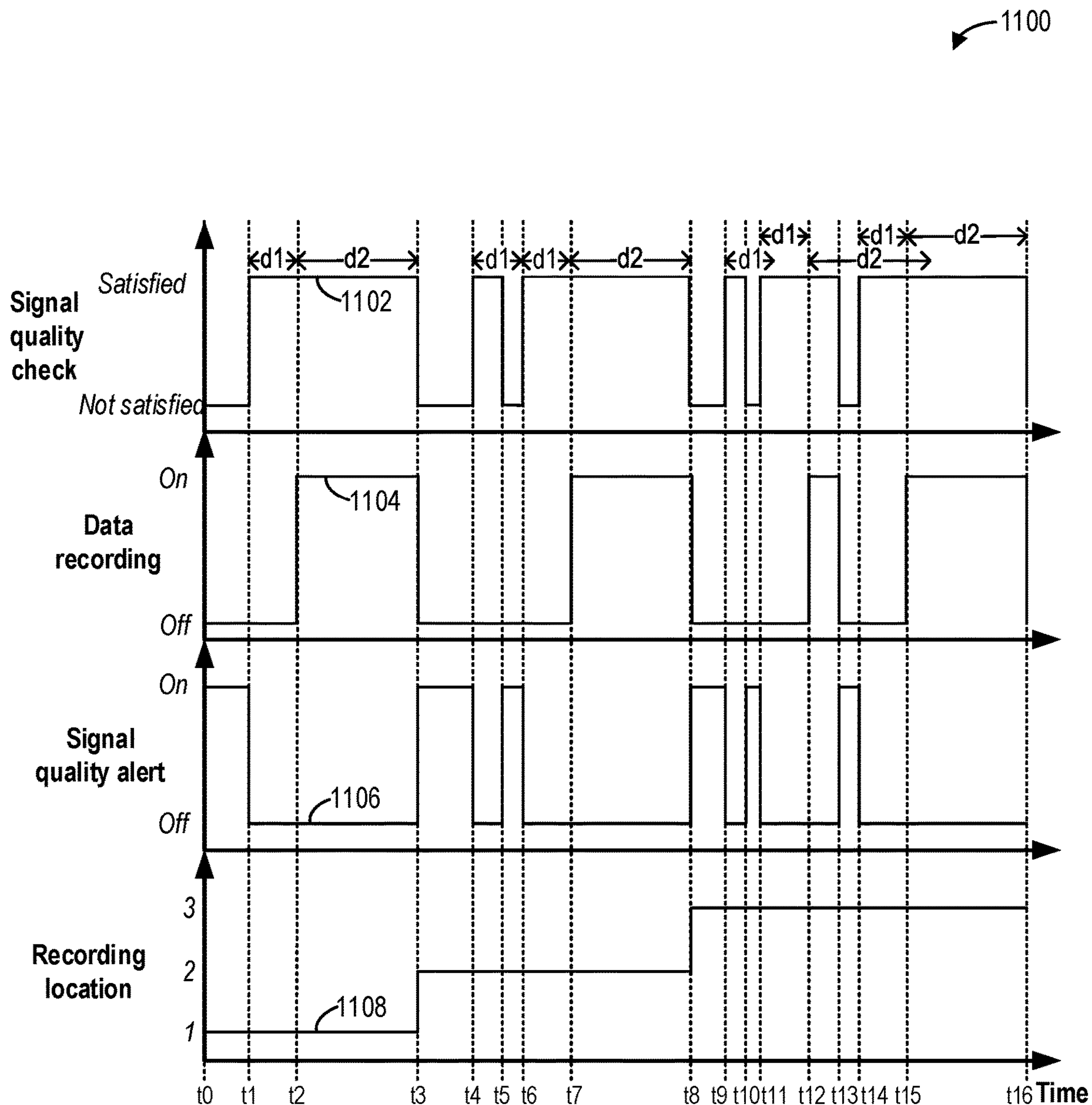
FIG. 11 shows a second example timeline of an electronic stethoscope performing a medical exam.

Additionally, various example displays that may be shown during a medical exam are shown in FIGS. 6-9. For example, FIG. 6 shows a display screen of a remote clinician and display screen of an electronic stethoscope user (e.g., the patient) during a synchronous exam where the clinician and patient are in real-time communication with each other. FIG. 7 shows an example display screen of the patient during an asynchronous exam where the clinician and the patient are not in real-time communication and the clinician may review the recorded physiological data at a later time. FIGS. 8A and 8B show an example patient display of the external computing device while the electronic stethoscope is in an incorrect placement (FIG. 8A) versus a correct placement (FIG. 8B). An example of acquiring physiological data at different locations during a single exam is shown in FIG. 9. Furthermore, two different example timelines for a medical exam signal quality check are shown in FIGS. 10 and 11.

Turning now to the figures, FIG. 1A shows a top view of an electronic stethoscope 100 comprising a housing 105, which encases sensors and control circuitry. The shape and design of the housing 105 may facilitate a subject's comfort during monitoring a state or condition of the subject. Additionally, the shape and design of the housing 105 may facilitate a secure fit against a variety of patient body types and shapes in order to increase sensor contact and with adequate sensor geometry.

The electronic stethoscope 100 may comprise one or more sensors. In some examples, the electronic stethoscope 100 comprises at least three sensors (e.g., sensor modalities). The sensors may be various types of sensors, such as ECG sensors, audio sensors, temperature sensors, pressure sensors, vibration sensors, force sensors, respiratory monitors or sensors (e.g., a device, device part, or sensor capable of measuring a respiration rate), heart rate monitors or sensors, intrathoracic impedance monitors or sensors (e.g., a device, device part, or sensor capable of measuring an intrathoracic impedance), accelerometers, and/or other types of sensors. The sensors may be part of the electronic stethoscope 100. In other examples, the sensors may be coupled with or otherwise configured to be used in combination with the electronic stethoscope 100.

The electronic stethoscope 100 comprises an electrical sensor 110 of a first sensor modality and an audio sensor 112 of a second sensor modality positioned on an exterior of the housing 105. In the illustrated example, the electrical sensor 110 includes a first electrode 110A and a second electrode 110B, however, other numbers of electrodes are possible. For example, the electrical sensor 110 may include 4 electrodes. For example, the first electrode 110A and the second electrode 110B may be ECG transducer electrodes, which may measure electrical signals from a patient resulting from depolarization of the heart muscle during a heartbeat. In the illustrated example, the first electrode 110A and the second electrode 110B include contact pads for obtaining ECG data. The audio sensor 112 may comprise a surface for obtaining audio data. The audio sensor 112 may include one or more microphones units for collecting audio data.

Additionally or alternatively, the first electrode 110A and the second electrode 110B may comprise a current injection electrode and a voltage measurement electrode, respectively, for intrathoracic impedance measurements. For example, each of the first electrode 110A and the second electrode 110B may be used to measure both electrocardiogram (ECG) and intrathoracic impedance. Measuring intrathoracic impedance may provide information about a presence or the amount of a fluid in the lungs of the subject. For example, intrathoracic impedance may decrease as an amount of a fluid in the lung or lungs increases. The reason for this may be that the fluid may conduct electrical current. Data collected using intrathoracic impedance sensors may provide insight and information about the condition of the lungs of the subject and identify potential signs of decompensation, pulmonary edema, or any state or condition of the subject correlated with the presence of fluid in lungs. For example, wheezes, crackles and rhonchi are often heard in lung sounds due to fluid accumulation in the lungs. Therefore, the intrathoracic impedance measurement may be used in conjunction with lung sounds obtained by the audio sensor 112 to provide a joint measure of fluid retention.

It may be understood that additional sensor modalities may be positioned internal to the housing 105, such as a third sensor 150 schematically indicated by a dashed box. In one example, the third sensor 150 is an accelerometer. The accelerometer may comprise a three-axis accelerometer, which may provide information about the orientation and motion of the electronic stethoscope 100. The accelerometer may be rigidly affixed to a surface within the electronic stethoscope 100 so that the accelerometer does not move independently from the electronic stethoscope 100 as a whole. The accelerometer may be used to calculate an orientation of the electronic stethoscope 100 when the electronic stethoscope 100 is held stationary by a user, such as the subject or a healthcare professional. The orientation of the electronic stethoscope 100 may be used by an algorithm in combination with a shape of ECG data (e.g., as recorded by the electrical sensor 110) to predict an ECG vector being measured. Further, the motion of the electronic stethoscope 100 measured by the accelerometer may be used to gate recording of the EGC data and/or audio data. Further, in some examples, the accelerometer (e.g., the third sensor 150) may be used to measure the respiration rate.

The electronic stethoscope 100 may additionally comprise user controls such as a button 114. The button 114 may control the intensity of a monitored signal to be transmitted to a user. The button 114 may comprise a positive end and a negative end, such that when the positive end (e.g., a first end) of the button is depressed, a signal amplitude is increased, and when a negative end (e.g., a second end opposite the first end) of the button is depressed, the signal amplitude is decreased. The signal amplitude may comprise a volume of an amplified audio signal. The audio signal may be transmitted wirelessly to an earpiece of a user (such as a healthcare provider) or do another connected electronic device.

FIG. 1B shows a bottom view of the electronic stethoscope 100. The electronic stethoscope 100 may comprise additional user controls such as a button 120. In some examples, the button 120 may be used to stop and start measurement of data by the electronic stethoscope 100. The button 120 may be actuated by a user. It may be possible to stop or start measurement without actuating the button 120, such as by controlling collection through a computing device, as will be elaborated herein with particular reference to FIG. 4.

The electronic stethoscope 100 may be used to collect ECG data, audio data, intrathoracic impedance data, and/or orientation and motion data from a plurality of different locations or parts of a body of the subject, such as positions at and/or around a heart, lung, vein, or artery of the subject. In some examples, the electronic stethoscope 100 may further comprise more sensors, such as the sensors listed anywhere herein, which may be used to collect data from various parts of the subject's body. Data collection may be performed by placing the electronic stethoscope 100 or the one or more sensors at different positions adjacent to the body of the subject (e.g., in contact with the body, inside the body, or remote from the body) and using the electronic stethoscope 100 to take one or more measurements (e.g., collect ECG data, audio data, intrathoracic impedance data, orientation and motion data, or any other type of data) at each of at least a subset of the different positions at suitable time points and/or intervals for suitable durations of time.

The electronic stethoscope 100 may be mobile. For example, the electronic stethoscope 100 may be movable from one point to another. The electronic stethoscope 100 may be configured to be placed on and removed from a body of the subject. For example, the electronic stethoscope 100 may be placed on the body of the subject at a location in proximity to a heart, lung, or bowel of the subject. The electronic stethoscope 100 may not be implantable in the body of the subject. The electronic stethoscope 100 may be sufficiently light that it is easily transported from one location to another. For example, the electronic stethoscope 100 may weigh between 0.5 pounds and 10 pounds. As another example, the electronic stethoscope 100 may weigh less than 0.5 pounds.

The electronic stethoscope 100 may be sufficiently sized such that it may be easily transported from one location to another. The electronic stethoscope 100 may be handheld, and as such, may be sized to fit in a hand. For example, the electronic stethoscope 100 may comprise an external dimension between about 0.25 inches and about 12 inches. In another example, the external dimension may be less than 0.25 inches.

Figure 2:
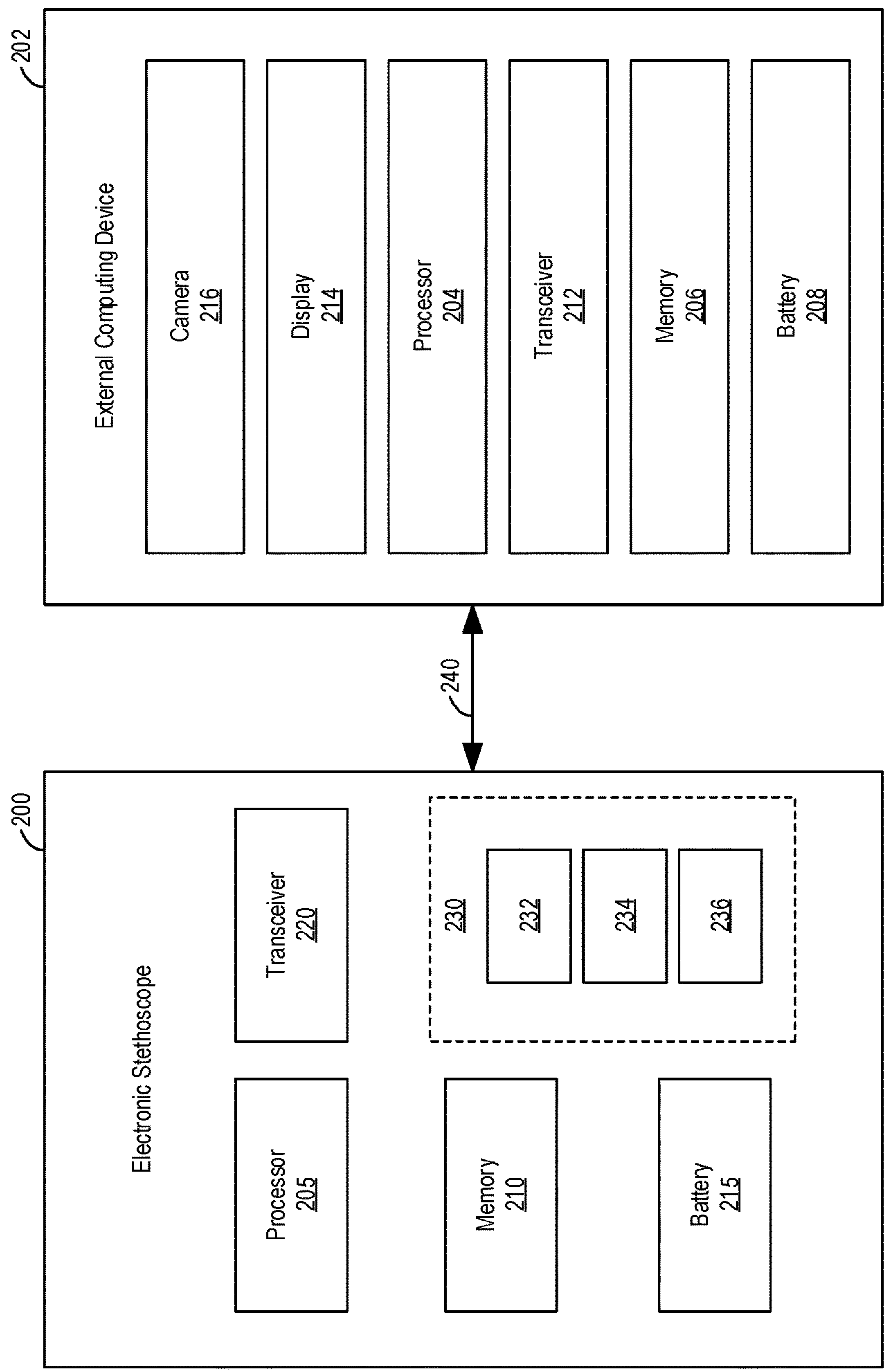
FIG. 2 shows a schematic of an interior of an electric stethoscope and an interior of an external computing device, both in communication with each other.

Turning now to FIG. 2, a schematic of an interior of an electronic stethoscope 200 and an interior of an external computing device 202 in communication with the electronic stethoscope 200 are shown. For example, the electronic stethoscope 200 may be the electronic stethoscope 100 shown in FIGS. 1A and 1B, or may be a similar monitoring device with capabilities of recording various physiological data and communicating with other electronic devices, such as the external computing device 202. As another example, the external computing device 202 may be a desktop computer, a laptop computer, a cellular phone, a tablet, or another device that includes a display and a capacity to communicate with other electric devices.

The electronic stethoscope 200 may comprise electrical components configured to control the operation of the various sensors. For example, the electronic stethoscope 200 may comprise devices to store data (e.g., hard drive or memory), to transmit data, to convert analog data to digital data, to provide information on the functionality of the monitoring device, to control various aspects of data collection, etc. The electronic stethoscope 200 may comprise a microprocessor or microprocessing unit (MPU) 205, also referred to as processor 205. The processor 205 may be operably connected to a memory 210. The processor 205 can execute a sequence of machine-readable instructions, which can be embodied in a program or software. The instructions can be directed to the processor 205, which can subsequently implement the methods or portions of the methods of the present disclosure. Power may be supplied to the various components (the sensors, the microprocessors, the memory, etc.) by a battery 215. The battery 215 may be coupled to charging circuitry, which may be wireless charging circuitry.

The electronic stethoscope 200 may transmit data to the external computing device 202 (e.g., a computing device that is external to the electronic stethoscope 200), another computing device, and/or to a network (e.g., to the cloud). The electronic stethoscope 200 may comprise a transceiver 220, such as a wireless transceiver, to transmit data to the computing device. The electronic stethoscope may be connected to the Internet. The monitoring device may be connected to a cellular data network and/or the Internet. The transceiver 220 may comprise a Bluetooth transceiver, a Wi-Fi radio, etc. Various wireless communication protocols may be utilized to convey data.

The electronic stethoscope 200 may store data (e.g., ECG data, audio data, and/or data from any combination of the one or more sensors and/or any of the sensor modalities) locally on the electronic stethoscope 200. In an example, the data may be stored locally on the memory 210 (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming.

The electronic stethoscope 200 includes a sensor unit 230. The sensor unit 230 may comprise an ECG transducer package 234 including an electrical sensor (e.g., the electrical sensor 110 shown in FIG. 1A) and an analog-to-digital converter (ADC) to digitize ECG signals detected by the ECG electrodes. The ECG data may comprise single-lead ECG data. Single-lead ECG data may be obtained from one electrode that may be a ground and another electrode that may be a signal electrode. The voltage difference between the two leads may comprise analog ECG signal data. ECG data can be recorded as voltage as a function of time. As an alternative, the ECG data may comprise three-lead ECG data. In still other examples, the EGC data may be obtained via more than three leads (e.g., five-lead ECG data).

In some examples, the ECG data may comprise chest cavity, lung, and/or intrathoracic impedance measurement data. The electrical data may comprise ECG data measured from a heart, lung, or other organ of a subject. The electrical data may comprise impedance data measured from a lung or intra-thorax of a subject (e.g., intrathoracic impedance data). The electrical data may comprise ECG data measured from a bowel or other organ of a subject.

The sensor unit 230 additionally includes an audio transducer package 232 and an accelerometer 236, which may be similar or the same as the third sensor 150 shown in FIG. 1A. The audio transducer package 232 may include an analog-to-digital converter to digitize audio signals detected by the audio sensor. The audio transducer package 232 may be used to record physiological sounds from the heart, lungs, stomach, etc. of a patient during an auscultation examination.

The electronic stethoscope 200 may be in communication with the external computing device 202 through a communication link 240. The communication link 240 may be a Bluetooth connection, internet connection, radio connection, or another type of connection that allows data to transfer between the electronic stethoscope 200 and the external computing device 202. For example, the electronic stethoscope 200 may record physiological sounds using the audio transducer package 232, and then the transceiver 220 may send the physiological data to the external computing device 202 through the communication link 240. The external computing device 202 may then receive the data by a transceiver 212. The transceiver 212 may comprise a Bluetooth transceiver, a Wi-Fi radio, etc. Various wireless communication protocols may be utilized to convey data.

The external computing device 202 may also include, but is not limited to, a camera 216, a display 214, a processor 204, a memory 206 (e.g., read-only memory, random-access memory, flash memory), and a battery 208. The battery 208 may supply power to the various components (the display 214, the memory 206, etc.). The battery 208 may be coupled to wireless charging circuitry, or may be charged using a charging wire. The processor 204 may comprise a microprocessor or MPU. The processor 204 may be operably connected to the memory 206. The processor 204 can execute a sequence of machine-readable instructions, which can be embodied in a program or software. The instructions can be directed to the processor 204, which can subsequently implement methods or components of methods of the present disclosure, such as a method to guide a patient through an auscultation examination, as will be described with reference to FIG. 3. The display 214 may show data collected by and transmitted from the electronic stethoscope 200. For example, the display 214 may show a shape of an ECG waveform to the user. As another example the display 214 may show an application that may guide the user through auscultation examinations. Examples of such displays are shown in FIGS. 6-9C. Additionally, the display 214 may include a user interface that allows the user to interact with the external computing device 202 such as through a touchscreen or other methods.

The camera 216 may include one or more lenses positioned in one or more locations on a surface of the external computing device 202, such as one or more front-facing cameras and one or more back-facing cameras. The camera 216 may include one or more optical (e.g., visible light) cameras, one or more infrared (IR) cameras, or a combination of optical and IR cameras having one or more view angles. For example, the camera 216 may include a first lens that directs light to a first, visible light image sensor (e.g., a charge-coupled device or a metal-oxide-semiconductor) and a second lens that directs light to a second, thermal imaging sensor (e.g., a focal plane array), enabling the camera 216 to collect light of different wavelength ranges for producing both visible and thermal images. In some examples, the camera 216 may further include a depth camera and/or sensor, such as a time-of-flight camera or a LiDAR sensor. In some examples, the camera 216 may be a digital camera configured to acquire a series of images (e.g., frames) at a programmable frequency (e.g., frame rate) and may be electronically and/or communicatively coupled to the processor 204. Further, the camera 216 may output acquired images to the processor 204 and/or the display 214 in real-time so that they may be processed in real-time by the processor 204, as will be elaborated herein with particular respect to FIG. 3.

As used herein, the term “real-time” refers to a process executed without intentional delay. For example, “real-time” may refer to a response time of less than or equal to about 1 second, a tenth of a second, a hundredth of a second, a millisecond, or less. In some examples, “real-time” may refer to simultaneous or substantially simultaneous audio or visual data generation, processing, and transmission.

Turning now to FIG. 3, an example method 300 for guiding a user through a medical examination is shown. For example, the medical exam may be an auscultation exam or an ECG performed using an electronic stethoscope, such as the electronic stethoscope 100 shown in FIGS. 1A-1B. At least a portion of the method 300 may be executed on a computing device that is external to the electronic stethoscope, such as the external computing device 202 shown in FIG. 2. The method 300 and the rest of the methods included herein may be executed by one or more processors, including a processor of the computing device (e.g., the processor 204 of FIG. 2), based on instructions stored on a memory operatively coupled to each of the one or more processors (e.g., the memory 206 of FIG. 2) and in conjunction with signals received from electronic components of the electronic stethoscope and the computing device. The computing device may be a desktop or laptop computer, a cellular phone, a tablet, or other computing device capable of connecting to other electronic devices, including the electronic stethoscope. Furthermore, the method 300 may be executed as part of a software application stored within the computing device that enables the user to interface with the electronic stethoscope wirelessly from the computing device.

At 302, the method 300 includes connecting to the electronic stethoscope. The computing device may connect to the electronic stethoscope through a wireless connection, such as Bluetooth, Wi-fi, radio, etc. Alternatively, the computing device may connect to the electronic stethoscope via a wired connection, such as Ethernet, universal serial bus (USB), etc. The connection may place the computing device and the electronic stethoscope in electronic communication with each other. For example, the electronic stethoscope may transmit data to the computing device. As another example, the computing device may transmit commands to the electronic stethoscope, examples of which will be elaborated below. As a further example, the (first) computing device may be connected to a second computing device. For example, the second computing device may be remote from the first computing device. As one example, the second computing device may be operated by a telemedicine clinician.

At 304, the method 300 includes obtaining live (e.g., real-time) images of the user via a camera. For example, the camera may be integral to the computing device (e.g., the camera 216 of FIG. 2), or the camera may be an external camera that is operatively coupled to the computing device. The live images of the user may include full body images of the front of the user or may include images of the user from a torso and above of the user. Additionally, the computing device may prompt the user (e.g., via a visual message on a display of the computing device or an audio prompt) to stand or sit a distance away from the camera so that the camera may obtain the desired images of the user (e.g., images showing a desired location for physiological data collection). For example, the computing device may instruct the user to get closer or farther from the camera. As another example, the computing device may display a generic silhouette of a body or a part of a body and instruct the user to generally position their body within the silhouette.

At 306, the method 300 includes tracking movement of the user and the electronic stethoscope. For example, the computing device may use computer vision in combination with tracking technology to track the movement of the user and the electronic stethoscope. The computer vision may differentiate a human (e.g., the user) from a background and identify a position of a number of features or joints, such as shoulders, elbows, and hands. Once the features are identified, the software may connect them into a humanoid skeleton and track their position in real-time, for example, using skeletal tracking. If the camera is a depth camera (e.g., a camera with pixels to measure depth), the computer vision may be able to disambiguate overlapping or occluded objects or limbs. The depth camera may also increase the robustness of the computer vision to different lighting conditions compared with a 2D camera-based algorithm. Additionally, the tracking technology may be used to identify and track a position of the electronic stethoscope.

At 308, the method 300 includes virtually displaying (e.g., via augmented reality) a placement indicator (e.g., device outline) on the live images of the user at a desired recording location. As one example, the live images may be displayed as a mirror image of the user, such as a mirror image video feed. In another example, the live images may be displayed as a real-time silhouette of the user that removes identifying features and details of the user to increase privacy. The desired recording location comprises an anatomical area for gathering physiological data during the medical examination. For example, the placement indicator may be positioned on or near the heart, lungs, stomach, etc. Further, the placement indicator may be angled optimally for obtaining the physiological data of interest. As another example, the medical examination may include more than one recording location, and so the placement indicator may be positioned at a currently desired recording location. For example, the currently desired recording location may be an initial (e.g., first) recording location at the beginning of the medical examination and a different, subsequent (e.g., second) recording location after data has already been acquired at the initial recording location.

The processor may determine the position for the placement indicator based on the desired recording location and an analysis of the user from the real-time images. For example, the processor may map the desired recording location to the unique physique and anatomy of the user using computer vision. Furthermore, using the skeletal tracking, the placement indicator may move as the user moves such that the placement indicator is at a fixed location on the user. The placement indicator may be shown as a same size as the electronic stethoscope appears in the live images. For example, the placement indicator may increase or decrease in size as the user moves towards or away from the camera, respectively, to accommodate for the size of the user and the electronic stethoscope increasing or decreasing in the live images. Thus, the user may be able to match the placement of the electronic stethoscope to the placement indicator.

At 310, the method 300 includes determining if a correct placement of the electronic stethoscope is detected. By tracking the position of the electronic stethoscope, the computing device is able to determine if the electronic stethoscope overlaps with the placement indicator. The correct placement may refer to a position of the electronic stethoscope that substantially fully overlaps with the placement indicator. For example, the computing device may use a real-time analysis algorithm to compare the position of the electronic stethoscope, as captured in the live images, with the position of the placement indicator and determine (e.g., calculate) a percentage of overlap. The computing device may determine that the electronic stethoscope is placed correctly in response to the percentage of overlap between the electronic stethoscope and the placement indicator being at least a threshold percentage. For example, the threshold percentage may be in a range from 90-100%. As one non-limiting example, the threshold percentage is 95%. In such an example, it may be determined that the electronic stethoscope is in the correct placement in response to the percentage of overlap being 95% or more, whereas it may be determined that the electronic stethoscope is not in the correct placement in response to the percentage of overlap being less than 95%.

Additionally or alternatively, the computing device may determine that the electronic stethoscope is placed correctly in response to a distance of the electronic stethoscope from the placement indicator being less than a threshold distance. The threshold distance may be to a non-zero distance that is stored in memory. Further, the distance may be a Euclidean distance or may be calculated via a plurality of positional parameters, including an angle of the electronic stethoscope compared to an angle of the placement indicator.

If the correct placement is not detected, the method 300 continues to 312 and includes outputting a position adjustment alert. The position adjustment alert may be output as a visual message, an audio message, and/or haptic feedback. For example, the visual message may include a text box or symbol shown on the display of the computing device. The text box may include a written message stating that the electronic stethoscope is placed incorrectly. In some examples, the message may further include instructions for moving the electronic stethoscope toward the correct placement, such as "move to the left" or "rotate to the right." As another example, the visual message may additionally or alternatively include the placement box remaining a color indicative of an incorrect placement (e.g., red) until a correct placement of the electronic stethoscope is detected, at which time the placement box may turn to a color indicative of a correct placement (e.g., green). As another example, the audio message may include an alert tone or tones and/or a voice message (which may be pre-recorded or computer generated) that indicates an incorrect placement of the electronic stethoscope. In some examples, the voice message may further include instructions for moving the electronic stethoscope toward the correct placement, such as described above. As a further example, the haptic feedback may include a vibration of the electronic stethoscope or computing device.

Returning to 310, if the correct placement is detected, the method 300 continues to 314 and includes automatically acquiring physiological data responsive to passing a signal quality check. As will be described in further detail with respect to FIG. 4, the signal quality check is used to determine whether the physiological data is of a high enough quality to be used for diagnostic or other medical purposes. For example, even if the correct placement is visually detected, the user may not be applying adequate force. As another example, ECG data quality may be affected by body hair, subcutaneous tissue, skin type, etc. If the physiological data passes the signal quality check, the computing device may record the physiological data from the electronic stethoscope. Thus, in response to the correct placement being detected, the computing device may instruct or command the electronic stethoscope to begin sampling data for the signal quality check.

At 316, the method 300 includes determining if an additional recording location is desired. For example, the medical examination may have a preset number of desired recording locations. As a further example, there may be 1, 2, 3, 4, or more recording locations desired. For example, the number and positions of the desired recording locations may be predetermined by the clinician or other telehealth professional prior to the onset of the exam. As another example, the computing device may contain a plurality of preset medical examinations that each include predetermined recording locations. The user (e.g., under guidance from the clinician) may select the appropriate preset medical examination from the plurality of preset medical examinations at the onset of the exam. It may be determined that an additional recording location is desired until the computing device has received physiological data for all of the desired recording locations.

In response to an additional recording location being desired, the method 300 continues to 318 and includes prompting the user to adjust the placement of the electronic stethoscope to the next recording location. For example, the computing device and/or the electronic stethoscope may output an adjustment alert similar to that described above at 312. For example, the user may be prompted with an audio message, or a visual message on the display, and/or haptic feedback. For example, the visual message may include a written message instructing the user to adjust the electronic stethoscope to the next recording location and/or the placement box changing colors. As another example, the haptic feedback may include a different vibration pattern or intensity than used for the position adjustment alert (e.g., at 312).

The method 300 may then return to 308, which includes virtually displaying the placement indicator on the live images of the user at the current desired recording location. The placement indicator location on the user is updated to the current desired recording location so that correct placement can again be assessed (e.g., at 310) and physiological data acquisition started (e.g., at 314) response to passing the signal quality check. As an example, if the previous recording location was proximate to the heart and the new recording location is proximate to the stomach, the placement indicator would no longer be displayed near the top left of the user's torso and instead appear near the bottom center of the user's torso. Examples of the placement box in various positions is shown in FIGS. 9A-9C.

Returning to 316, if an additional position is not desired, the method 300 continues to 322 and includes signaling the end of the exam to the user. For example, the computing device may signal the end of the exam by no longer displaying the live images of the user. Additionally or alternatively, the computing device may output a visual message, an audio message, or haptic feedback indicating the medical examination has ended. For example, the haptic feedback may include a different vibration pattern or intensity than for the position adjustment alert and/or for adjusting placement to the next recording location. The method 300 may then end.

In this way, a user (e.g., a patient) may be guided through a medical examination in situations where a clinician is not able to perform the examination in person. For example, the method 300 may be used in instances where it is desired to maintain distance between the patient and the clinician, such as in cases of infectious diseases. As another example, the method 300 may be used for telehealth appointments where the patient and the clinician are located remotely from each other. By tracking the user through the computing device, an accurate placement of the electronic stethoscope may be achieved. Thus, accuracy quality of recorded physiological data may be increased, which may in turn increase an accuracy of a resulting diagnosis by the clinician evaluating the recorded physiological data.

Referring now to FIG. 4, a method 400 for automatically recording physiological data with an electronic stethoscope responsive to a signal quality check being satisfied is shown. The electronic stethoscope may be the electronic stethoscope 100 shown in FIGS. 1A-1B and/or the electronic stethoscope 200 shown in FIG. 2. The method 400 may be executed by one or more processors, including a processor of the electronic stethoscope (e.g., the processor 205 of FIG. 2), based on instructions stored on a memory operatively coupled to each of the one or more processors (e.g., the memory 210 shown in FIG. 2) and in conjunction with signals received from electronic components of the electronic stethoscope. The method 400 may be performed as a part of the method 300 of FIG. 3 (e.g., at 314). As another example, the method 400 may be executed independently from method 300 of FIG. 3, such as by a trained clinician who chooses not to use the visual guidance provided by method 300 of FIG. 3. For example, the electronic stethoscope may be operated in a first mode that includes performing the signal quality check after visually guiding placement of the electronic stethoscope via augmented reality (e.g., when method 400 is performed as a part of method 300 of FIG. 3) or operated in a second mode that includes performing the signal quality check without visually guiding the placement of the electronic stethoscope (e.g., when method 400 is executed independently from method 300 of FIG. 3).

At 401, the method includes connecting to an external computing device. The external computing device may be the external computing device 202 shown in FIG. 2, for example. In examples where the method 400 is performed as a part of method 300 of FIG. 3, the external device may be performing at least parts of the method 300. In such an example, 302 of the method 300 and 401 of the method 400 may be performed simultaneously. Further, when the electronic stethoscope is already connected to the external computing device, 401 may be omitted.

The electronic stethoscope may connect to the external computing device through a wireless connection, such as Bluetooth, Wi-fi, radio, etc. Alternatively, the electronic stethoscope may connect to the computing device via a wired connection, such as Ethernet, universal serial bus (USB), etc. The connection may place the electronic stethoscope and the external computing device in electronic communication with each other. For example, the electronic stethoscope may obtain physiological data and transfer the data to the external computing device. As another example, the external computing device may inform the electronic stethoscope of a current recording location so that the electronic stethoscope, which may be utilized for performing the signal quality check, as will be elaborated below. For example, a clinician may input selections regarding desired recording locations, a type of medical examination being performed, a medical examination protocol, etc. via a user interface of a software application that is executed on the external computing device.

At 402, the method includes acquiring physiological data for a signal quality check. For example, the physiological data may comprise audio data and/or ECG data, although other physiological data is also possible (e.g., intrathoracic impedance data). The physiological data may be obtained through the various sensors of the electronic stethoscope, such as those described above with respect to FIGS. 1A and 1B. For example, electrodes of the electronic stethoscope (e.g., the first electrode 110A and the second electrode 110B shown in FIG. 1A) may acquire ECG data. As another example, the electronic stethoscope may obtain audio data via an audio sensor (e.g., the audio sensor 112 shown in FIG. 1A). The electronic stethoscope may continuously acquire data for the signal quality check at a desired sampling frequency (or rate). For example, the electronic stethoscope may sample data for 1, 2, 3, 4, or more seconds and may acquire a plurality of samples.

At 404, the method includes performing the signal quality check as the physiological data is acquired for the signal quality check. That is, each sample of the physiological data may be analyzed as it is acquired such that a first, initial sample is analyzed as a second, subsequent sample is acquired, and so on. The signal quality check may utilize a machine learning algorithm to determine whether the physiological data is of a high enough quality to be clinically relevant. For example, the machine learning algorithm may be trained using examples of both high quality data that passes the signal quality check and low quality data that does not pass the signal quality check for each recording location, enabling the location-specific evaluation of the physiological data. For example, the signal quality check may evaluate for location-specific data patterns as well as a signal-to-noise ratio. For example, physiological data meant for cardiac auscultation may evaluate the physiological data against heart sound signal quality metrics (e.g., a model trained using high quality data and low quality data from the heart), whereas physiological data meant for pulmonary auscultation may be evaluated against lung sound signal quality metrics. For example, a model used for evaluating the physiological data may be selected from a plurality of stored models encompassing all of the possible recording locations so that the selected model is specific to the current recording location. As such, the physiological data will only be evaluated using the selected, location-specific model.

At 406, the method 400 includes determining if the signal quality check is satisfied. As one example, the signal quality check may be considered satisfied when the physiological data satisfies a signal quality threshold. The signal quality threshold may be stored within a memory of the electronic stethoscope or the external computing device. For example, the machine learning algorithm may consider multiple parameters, such as the signal amplitude and whether the signal is correct for the recording location and type of data being acquired, in determining whether the physiological data satisfies the signal quality threshold. As a further example, the signal amplitude may be compared to an amplitude threshold. For example, the amplitude threshold may be a non-zero number stored within the memory and corresponds to a signal amplitude above which the physiological data signal is considered to be strong enough for clinical use. Further, the amplitude threshold may be specific to the type of physiological data being recorded such that different physiological data types may include different amplitude thresholds.

As a further example, the signal quality check may be satisfied in response to the physiological data satisfying the signal quality threshold for at least a threshold duration and/or for at least a threshold number of sequential samples. The threshold duration and the threshold number of sequential samples may be non-zero values stored in the memory that indicate that the physiological data quality is steady. For example, the threshold duration may be a time value in a range from 3 to 10 seconds. As a non-limiting example, the threshold duration may be 6 seconds. Using the above example, the signal quality check may be considered satisfied in response to the physiological data satisfying the signal quality threshold for 6 continuous seconds. In contrast, the signal quality check may not be considered satisfied in response to the physiological data not satisfying the signal quality threshold for 6 continuous seconds, such as by satisfying the signal quality threshold for 3 continuous seconds before no longer satisfying the signal quality threshold. As another example, the threshold number of sequential samples may be in a range from 2 to 5 samples (e.g., 3 samples). Thus, the signal quality check may be considered satisfied in response to the physiological data satisfying the signal quality threshold in 3 sequential samples. In contrast, the signal quality check may not be considered satisfied in response to the physiological data not satisfying the signal quality threshold in 3 sequential samples, such as by satisfying the signal quality threshold in 2 sequential samples before no longer satisfying the signal quality threshold.

Figure 5:
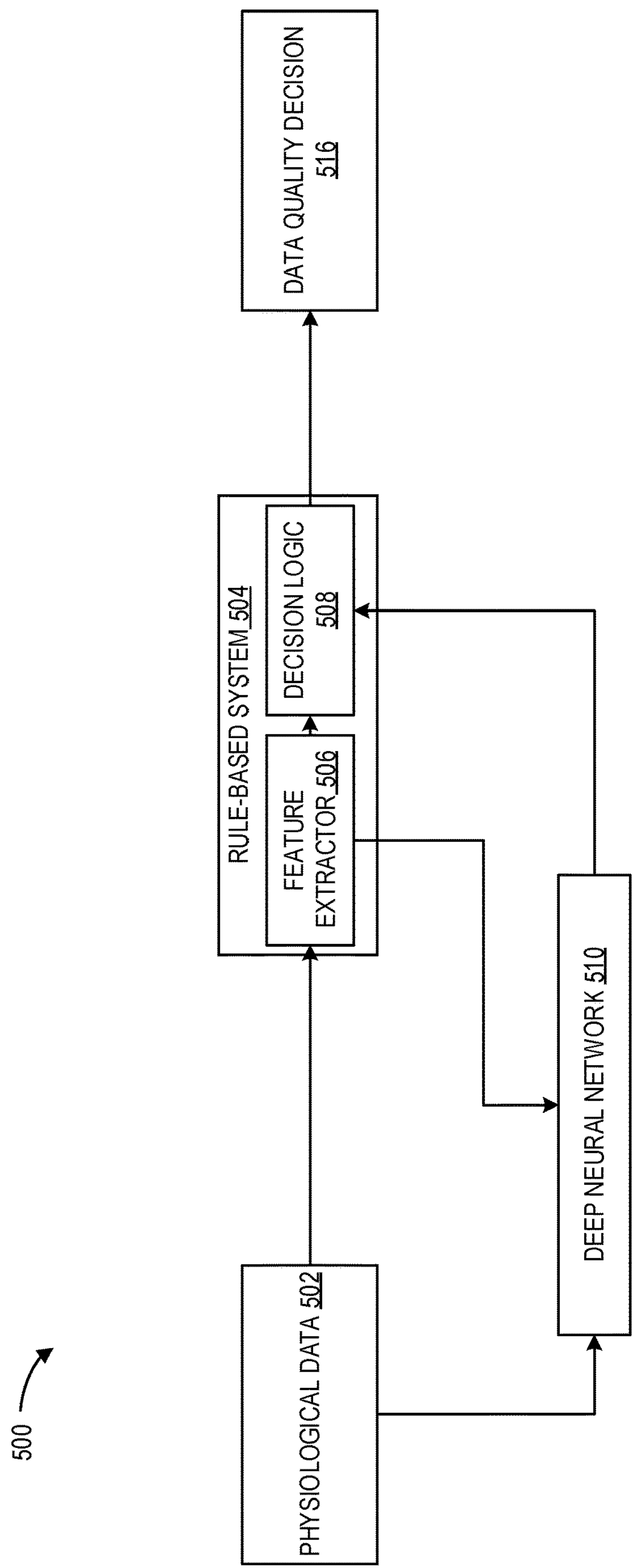
FIG. 5 shows a schematic diagram illustrating a machine learning diagnostic system for physiological data.

Referring briefly to FIG. 5, an example machine learning algorithm 500 is shown. Physiological data 502 is input into both a feature extractor 506 of a rule-based system 504 and a deep neural network 510. The feature extractor 506 may identify features of the physiological data. When the physiological data 502 includes audio data, the features may include, for example, a type of audio signal (e.g., a heartbeat, murmur, crackle, wheeze), a frequency of the given signal, an amplitude of the given signal, etc. When the physiological data includes ECG data, the features may include, for example, segments and intervals of the ECG waveform (e.g., PR interval, QT interval, QRS complex), a vector of the ECG waveform, an amplitude of the ECG waveform, etc.

The feature extractor 506 outputs the identified features into the decision logic 508 of the rule-based system 504. Thus, the machine learning algorithm receives either one or both of the deep neural network 510 acting on the physiological data 502 and the decision logic 508 acting on the extracted features from the feature extractor 506. The deep neural network 510 may employ pattern recognition developed via data set training, such as the training described above, with respect to 404 of FIG. 4, to further recognize the type of data and recording location of the physiological data.

The decision logic 508 determines if the physiological data 502 is a high enough quality to be clinically relevant using a plurality of rules. For example, the decision logic 508 may compare the identified recording location to a desired recording location and an overall signal-to-noise ratio to a threshold signal-to-noise ratio and make a decision regarding the quality of the data and output a data quality decision 516. For example, the data quality decision 516 may state whether or not the physiological data 502 satisfies the signal quality check described with respect to 406 of FIG. 4.

Returning to FIG. 4, if the signal quality check is not satisfied at 406, the method 400 continues to 408 and includes outputting a signal quality alert. The signal quality alert may be a visual message, an audio message, and/or haptic feedback. As one example, the visual message may include a fluctuating light bar that changes based on the signal quality (e.g., a longer light bar indicates increasing signal quality) and/or may change colors to specify a passing (e.g., green) or a not passing (e.g., red) signal quality. As another example, the visual message may include a text-based message that may be output on a display, such as a display of the external computing device. The audio message may include one or more tones and/or a spoken message. In some examples, the text-based message and/or the audio message may include information regarding why the physiological data did not pass the signal quality check (for example, "low signal amplitude," "incorrect recording location," "recording location could not be verified") and/or instructions for increasing the signal quality (for example, "adjust electronic stethoscope position," "increase pressure," "apply conductive gel," etc.). The method 400 may then end.

Returning to 406, in response to the signal quality check being satisfied, the method 400 continues to 410 and includes recording physiological data for the examination. The electronic stethoscope may record the physiological data by storing it in the memory of the electronic stethoscope. In another example, the electronic stethoscope may transmit the physiological data to the external computing device in real-time, and the external computing device may store the recording. Further, the physiological data may be recorded for a pre-determined duration and may include acquiring a larger amount of data than used for the signal quality check. As one example, the pre-determined duration may be a time value in a range from 10 to 30 seconds. As a non-limiting example, the pre-determined duration may be 15 continuous seconds. In some examples, the pre-determined duration may vary based on the recording location and/or exam type. For example, the pre-determined duration may be longer or shorter for recording heart sounds versus lung sounds. As another example, the pre-determined duration may be longer or shorter for ECG data relative to audio data. Alternatively, the pre-determined duration may be the same for every recording location. In some examples, the clinician may adjust the pre-determined duration, such as via inputs to the software application on the external computing device.

Further, the signal quality may continue to be evaluated in parallel as the physiological data is recorded for the exam. Therefore, at 412, the method 400 includes determining if the signal quality check is satisfied. Thus, even after the signal quality check is satisfied to commence recording, the signal quality check may be performed during the recording in real-time. The signal quality check may be performed as described above at 406.

If the signal quality check is not satisfied at 412, the method 400 continues to 408, which includes outputting the signal quality alert, as described above. Further, if the pre-determined duration of physiological data has not been recorded prior to the signal quality check no longer being satisfied, the processor may not store the incomplete recording. As another example, the processor may overwrite the incomplete recording of the physiological data upon the method 400 being repeated and the recording being initiated in response to the signal quality check being satisfied (e.g., at 406).

Returning to 412, if the signal quality check continues to be satisfied, the method 400 continues to 414 and includes continuing to record the physiological data for the exam. For example, the physiological data may be recorded for the pre-determined duration for the given recording location. As such, the electronic stethoscope may stop recording the physiological data after the pre-determined duration has elapsed while the signal quality check continues to be satisfied.

The method 400 may then end. For example, the electronic stethoscope may be placed into a stand-by state (e.g., not actively performing the method). As another example, the method 400 may be repeated to record physiological data for the remaining locations specified by the selected medical examination protocol and/or selected recording locations.

Turning now to FIG. 6, an example of a synchronous remote medical examination 600 is shown. The electronic devices may each be examples of the external computing device 202 shown in FIG. 2. The synchronous remote medical examination 600 comprises a medical examination occurring while a patient is in real-time remote contact with a telemedicine provider (e.g., a clinician).

A patient view 602 and a clinician view 604 are shown. The patient view is displayed on a patient computing device 606 that includes a camera 630 and a display screen 640, while the clinician view 604 is shown on a display screen 642 of a clinician computing device 608 that includes a camera 632. The patient computing device 606 and the clinician computing device 608 each may be one example of the external computing device 202 of FIG. 2. The camera 630 of the patient computing device 606 may capture real-time, live images of the patient, which is shown as a patient image 610 on both the patient view 602 and clinician view 604. The camera 632 of the clinician computing device may capture real-time, live images of the clinician, which may be displayed in a clinician display box 605 shown on the display screen 640 of the patient computing device 606. For example, the clinician display box 605 may be an inset box within the patient image 610. In this way, the clinician may be able to provide additional assistance to the patient during the medical exam.

The patient computing device 606 and the clinician computing device 608 may be in communication with each other through communication link 615. The communication link 615 may be established through an internet connection (which may be wired or wireless), Bluetooth connection, radio connection, or other wireless connection. The clinician computing device 608 may be a same or different type of computing device as the patient computing device 606. For example, the patient computing device 606 may be a smartphone, and the clinician computing device 608 may be a tablet (or vice versa). The patient computing device 606 and the clinician computing device 608 may be any type of computing device including a display, a live streaming camera, and capable of forming the communication link 615.

Additionally shown on the clinician view 604 is a physiological data box 650 that may display a waveform 651 of physiological data acquired by an electronic stethoscope used to gather data for the synchronous remote medical examination 600. An image of the electronic stethoscope may be captured in the real-time images of the patient and shown in both the patient view 602 and the clinician view 604 as an electronic stethoscope image 612. The electronic stethoscope may be one example of the electronic stethoscope 100 introduced with respect to FIGS. 1A and 1B and/or the electronic stethoscope 200 introduced with respect to FIG. 2. In the example shown in FIG. 6, the waveform 651 is flat, as the electronic stethoscope is not placed on the patient.

The patient image 610 may be a silhouette or otherwise altered (e.g., facial blurring) to protect patient privacy or may use real-time images of the patient without alteration. The electronic stethoscope image 612 is shown being held by the patient image 610. In some examples, the electronic stethoscope image 612 may not be altered so as to stand out against the patient image 610. An augmented reality placement box 614 is shown on the patient image 610 and indicates a desired location for the electronic stethoscope to be placed. The augmented reality placement box 614 may be in different locations based on the physiological data that is desired to be obtained during the examination. Examples of different locations are shown in FIGS. 9A-9C.

The patient view 602 and the clinician view 604 may each also include a plurality of progress indicators including an initialization indicator 616, a first location indicator 618, a second location indicator 620, and a review indicator 622. The plurality of progress indicators inform both the patient and the clinician which portion of the exam is finished and which portion of the exam is yet to be performed. For example, the initialization indicator 616, which may be used to indicate a connection between the electronic stethoscope and the patient computing device 606, is shown outlined with a solid line, indicating that portion of the examination has been performed. As another example, the first location indicator 618 is also shown with a solid line, indicating physiological data from a first location in the exam has been obtained. Indicators shown with dashed outlines, such as the second location indicator 620 and the review indicator 622, indicate that those portions of the exam are in process or are still desired to be performed. While two location indicators (e.g., the first location indicator 618 and the second location indicator 620) are shown, there may be more or fewer location indicators displayed based on the number of desired locations for the particular exam being performed. For example, there may be only one location desired for the synchronous remote medical exam 600, or there may be 2, 3, 4 or more locations desired, and the number of locations desired may be reflected by the amount of location indicators. Note that although solid lines and dashed lines are used to distinguish completed exam tasks and upcoming/in progress exam tasks in the present example, other visual differences may be used (such as color, typeface, opacity, etc.).

Turning now to FIG. 7, an example of a user and computer display for an asynchronous remote medical exam 700 is shown. Components of FIG. 7 that function the same as components previously introduced in FIG. 6 are numbered the same and will not be re-introduced. The asynchronous remote medical exam 700 may be done independently of a telemedicine provider or clinician. For example, a patient may be able to do the asynchronous remote medical exam 700 without additional guidance by a telemedicine professional or a clinician, and as such, the clinician display box 605 shown in FIG. 6 is omitted. The asynchronous remote medical exam 700 may be reviewed by a clinician after completion.

A patient view 706 shows what a patient 702 may see on the patient computing device 606 during the asynchronous remote medical exam 700. The patient 702 may use an electronic stethoscope 712, which may be the electronic stethoscope 200 of FIG. 2, for example. As described above with respect to FIG. 6, the camera 630 may take real-time images of the patient 702 and the electronic stethoscope 712, which may be shown on the display screen 640 as the patient image 610 and the electronic stethoscope image 612, respectively. In this way, the augmented reality placement box 614 may guide the patient 702 on the placement of the electronic stethoscope 712 throughout the medical examination without a clinician providing assistance in real-time. For example, as described above with respect to FIGS. 3 and 4, in response to the electronic stethoscope 712 being correctly placed within the augmented reality placement box 614 (e.g., the electronic stethoscope image 612 substantially fully overlaps with the augmented reality placement box 614), a signal quality check may be initiated, and the physiological data may be automatically recorded for the given location responsive to the signal quality check being satisfied.

Turning now to FIGS. 8A and 8B, examples of an incorrect placement 800 (FIG. 8A) and a correct placement 801 (FIG. 8B) are shown. Components of FIGS. 8A and 8B that function the same as components previously introduced in FIG. 6 are numbered the same and will not be re-introduced. Both FIGS. 8A and 8B provide examples of what may be shown on the display screen 640 while a patient is performing a synchronous medical exam (e.g., the synchronous remote medical exam 600) or an asynchronous medical exam (e.g., the asynchronous remote medical exam 700).

Beginning with FIG. 8A, the incorrect placement 800 shows the electronic stethoscope image 612 misaligned with the augment reality placement box 614. As a result, an incorrect placement indicator 805 is shown on display screen 640. In the example of FIG. 8A, the incorrect placement indicator 805 reads, "Incorrect Placement." However, other messages may be used. For example, the incorrect placement indicator 805 may read, "Adjust electronic stethoscope placement," and may include additional instructions to assist the patient to move the electronic stethoscope to the correct position, such as, "move the electronic stethoscope upwards." Furthermore, an audio message or other indicator (e.g., haptic feedback) may be used in addition to or as an alternative to the incorrect placement indicator 805. For example, the patient computing device 606 may include a speaker to audibly alert the patient of the incorrect position, such as via pre-recorded or generated messages, beeps or tones, etc.

Continuing now to FIG. 8B, if the electronic stethoscope is placed in a correct position (e.g., the electronic stethoscope image 612 is aligned with the augmented reality placement box 614) or moved to the correct position, a correct placement indicator 810 may appear on the display screen 640 as an additional indication to the patient that the electronic stethoscope is in the correct position. In the example of FIG. 8B, the correct placement indicator 810 reads, "Correct Placement." In other examples, the correct placement indicator 810 may display a different message than shown in FIG. 8B that conveys to the patient that the electronic stethoscope is in the correct position. Furthermore, an audio message or indicator and/or haptic feedback may be used in addition to or as an alternative to the correct placement indicator 810. For example, the speaker of the patient computing device 606 may audibly alert the patient of the correct position, such as via pre-recorded or generated messages, beeps or tones, or other sounds specially used to indicate that the position is correct.

Turning now to FIG. 9, an example sequence 901 of display outputs during a medical examination having multiple prescribed recording locations is shown. Although three recording locations are shown, there may be more or fewer than three recording locations in other examples. A first location is shown in a first display output 900, a second location is shown in a second display output 902, and a third location is shown in a third display output 904. Components of FIGS. 8A and 8B that function the same as components previously introduced in FIG. 6 are numbered the same and will not be re-introduced. For example, each of the first display output 900, the second display output 902, and the third display output 904 are shown on the display screen 640 of the patient computing device 606 during the medical examination. For example, the medical examination may be the asynchronous exam described with respect to FIG. 7 or the synchronous exam described with respect to FIGS. 8A and 8B.

The first display output 900 shows the first location as within the stomach region, as indicated by the position of the augmented reality placement box 614. However, the first location may be in another anatomical location in other examples, such as the heart, lungs, etc. Further, the patient image 610 shows the electronic stethoscope image 612 in a correct location, as indicated by the alignment of the electronic stethoscope image 612 with the augmented reality placement box 614. The initialization indicator 616 is outlined with a solid line, indicating that portion of the exam has been initialized (e.g., by confirming connection with the electronic stethoscope and connecting with a remote clinician if desired). As physiological data is currently being recorded at the first location, the first location indicator 618 is outlined with a dashed line in the first display output 900. Although not shown, in some examples, the first location indicator 618 may have additional features to indicate the exam is currently collecting data from the first location, such as the first location indicator 618 blinking, changing color, having a moving outline, etc.

A recording message 910 may be shown on the display screen 640 to indicate to the user that the electronic stethoscope is currently recording. In the example shown in FIG. 9, the recording message 910 states, "Recording: Do not Move." In other examples, the recording message 910 may include a different but similar message that the electronic stethoscope is recording physiological data and that it is desired to reduce movement and/or noise. In some examples, the recording message 910 may include a sound indicating the beginning and end of the recording and/or haptic feedback in addition to or as an alternative to the visual message. As a further example, lights on the display screen or included on the electronic stethoscope may indicate to the patient that the electronic stethoscope is recording.

The second display output 902 shows the second location as within the chest region, as indicated by the updated position of the augmented reality placement box 614. However, the second location may be in another anatomical location in other examples. The patient image 610 shows the electronic stethoscope image 612 in a correct location, as indicated by the alignment of the electronic stethoscope image 612 with the augmented reality placement box 614. Because the physiological data for the first location has been obtained, the first location indicator 618 is outlined in a solid line, indicating the physiological data for the first location has been collected. Due to the physiological data currently being acquired at the second location in the second display output 902, the outline of the second location indicator 620 is not solid. In the example shown in FIG. 9, the outline is dashed, but in other examples, the second location indicator 620 may include additional features to indicate the exam is currently in the second display output 902, as described above. Further, the recording message 910 again instructs the patient to remain still while the physiological data is recorded at the second location.

The third display output 904 shows the third location is in a different region of the chest, as indicated by the updated position of the augmented reality placement box 614. However, the third location may be a different anatomical area in other examples. Further, the patient image 610 shows the electronic stethoscope image 612 aligned with the augmented reality placement box 614. Because the physiological data has already been obtained at the first location and the second location, the first location indicator 618 and second location indicator 620 are both outlined with a solid line. Due to the physiological data for the third location actively being collected, a third location indicator 906 is shown with a dashed outline in the third display output 904. As described above, the third location indicator 906 may show additional or alternative features to indicate to the patient that the physiological data is currently being collected at the third location. As also described above, the recording message 910 instructs the patient to remain still while the physiological data is recorded at the third location.

Turning now to FIG. 10, a first exemplary prophetic timeline 1000 of a medical examination having multiple prescribed recording locations is shown. Physiological data for the medical exam may be obtained by an electronic stethoscope operated in a first mode, such as the electronic stethoscope 100 shown in FIGS. 1A and 1B, in connection with a computing device, such as the external computing device 202 shown in FIG. 2. For example, the electronic stethoscope may wirelessly connect with the computing device, and the computing device may employ augmented reality to guide a user in placing the electronic stethoscope at each recording location, such as described above with reference to FIGS. 3 and 6-9. A visual placement confirmation is shown in a plot 1002, a signal quality check is shown in a plot 1004, a data recording indicator is shown in a plot 1006, a signal quality alert is shown in a plot 1008, and a recording location indicator is shown in a plot 1010.

For all of the above, the horizontal axis represents time, with time increasing along the horizontal axis from left to right. Vertical lines at times t0-t15 represent time points of interest. The plots in FIG. 10 are time-aligned and occur at the same time. For plot 1002, the vertical axis indicates the visual placement confirmation as "yes" or "no." For example, if the visual placement confirmation is "yes," it is confirmed that the electronic stethoscope is in a correct location via live image capture of the user and the electronic stethoscope by the computing device. As a further example, if the visual placement confirmation is "no," the electronic stethoscope is determined to be in an incorrect location via the live image capture of the user and the electronic stethoscope. For plot 1004, the vertical axis indicates whether the signal quality check is satisfied, not satisfied, or is off, as labeled. For example, if the signal quality check is satisfied, then the physiological data obtained by the electronic stethoscope is of a high enough quality to be recorded for clinical purposes. In contrast, when the signal quality check is not satisfied, the physiological data obtained by the electronic stethoscope is not of a high enough quality to be clinically relevant. As another example, the signal quality check may be off when the visual placement confirmation is not confirmed such that the signal quality check is not performed when the electronic stethoscope is not in the correct location.

For plot 1006, the vertical axis indicates whether the electronic stethoscope data recording is "on" or "off." For example, recorded physiological data may be saved in a memory of the electronic stethoscope and/or a memory of the computing device. The electronic stethoscope may continuously sample physiological data for the signal quality check, but the electronic stethoscope may not record and/or transmit such data while the recording is off. For plot 1008, the vertical axis indicates whether the signal quality alert is "on" or "off." For example, the signal alert may be on when the signal quality check is not satisfied. As another example, the signal quality alert may be off when the signal quality check is satisfied or when the signal quality check is off. For plot 1010, the vertical axis indicates a recording location of the electronic stethoscope. For example, the electronic stethoscope may be in a first recording location (e.g., "1'), a second recording location (e.g., "2"), or a third recording location (e.g., "3"). Although only three locations are shown in the example timeline 1000, in other examples there may be more or fewer locations without departing from the scope of this disclosure.

Further, two different time durations will be referenced with respect to plot 1004: a first time duration d1 and a second time duration d2. The first time duration d1 refers to a threshold duration for the signal quality check to be satisfied before data recording (plot 1006) is initiated. The second time duration d2 refers to a pre-determined amount of high quality physiological data to record for each recording location. In the example of timeline 1000, the second time duration d2 is the same for all of the recording locations; however, in other examples, the pre-determined duration may vary based on the recording location and the type of physiological data obtained at each recording location.

The medical exam begins at time t0 at the first recording location (plot 1010). From time t0 to time t1, the visual placement of the electronic stethoscope (plot 1002) is not confirmed, indicating that the electronic stethoscope is not in a correct position for the first recording location. As a result, the signal quality check (plot 1004) is off, data is not being recorded (plot 1006), and the signal quality alert (plot 1008) is not issued. At time t1, in response to the electronic stethoscope being placed in the correct position, the visual placement of the electronic stethoscope is confirmed (plot 1002), and the signal quality check is no longer off. From time t1 to time t2, the signal quality check is satisfied for the first time duration d1 (plot 1004). In response, the data recording is initiated at time t2 (plot 1006).

The signal quality check remains satisfied from time t2 to time t3 (plot 1004), and so the data recording remains active (plot 1006). The second time duration d2 ends at time t4, and so the data recording is turned off (plot 1006). Because the recorded data passed the signal quality check throughout the second time duration d2, the signal quality alert remains off from time t2 to time t3 (plot 1008), and the recorded data may be saved to the electronic stethoscope or the computing device for further review by a clinician.

Because the data recording for the first recording location was successful, the exam continues to the second recording location at time t3, as indicated in plot 1010. From time t3 to time t4, the electronic stethoscope position is not visually confirmed (plot 1002) due to the user adjusting the position of the electronic stethoscope from the first recording location to the second recording location. At time t4, the electronic stethoscope position is visually confirmed (plot 1002), and in response, the signal quality check is commenced. However, the signal quality check is not satisfied at time t4 (plot 1004). As a result of the signal quality check not being satisfied, the signal quality alert is turned on at time t4, alerting the user that an adjustment should be made to obtain a quality signal. For example, the adjustment may include removing an article of clothing, increasing the pressure applied to the electronic stethoscope, applying a conductive gel, etc.

At time t5, the signal quality check changes from not satisfied to satisfied (plot 1004), resulting in the signal quality alert turning off (plot 1008). However, before the first time duration d1 elapses, the signal quality check changes from satisfied to not satisfied at time t6 (plot 1004), and the signal quality alert turns on (plot 1008) and remains on while the signal quality check is not satisfied. Further, because the signal quality check was not maintained satisfied for the first time duration d1, data recording is not commenced (plot 1006).

At time t7, the signal quality check is again satisfied (plot 1004). In response, the signal quality alert turns off (plot 1008). The signal quality alert remains satisfied for the first time duration d1, which lasts from time t7 to time t8. As a result, at time t8, data recording (plot 1006) commences at the second location. The signal quality check remains satisfied (plot 1004) for the second time duration d2 while the physiological data is recorded at the second recording location. As a result, when the second duration d2 elapses at time t9, the recorded data may be saved to the electronic stethoscope and/or the computing device.

Due to the data recording for the second recording location being successful, the exam continues to the third recording location at time t9, as indicated by plot 1010. At time t9, the placement of the electronic stethoscope (plot 1002) is not visually confirmed, which may be due to the user adjusting the placement of the electronic stethoscope. At time t10, the electronic stethoscope is in the correct position, and the placement is visually confirmed (plot 1002). In response to the visual confirmation, the signal quality check is assessed and is satisfied (plot 1004), and the first time duration d1 begins. At time t11, the first time duration d1 elapses with the signal quality check satisfied throughout the first time duration d1. As a result, data recording (plot 1006) commences at time t11.

However, at time t12, the signal quality check is no longer satisfied before the second time duration d2 elapses, resulting in the data recording being discontinued (plot 1006) and the signal quality alert (plot 1008) being output. Because the physiological data was not recorded for the entire second time duration d2, the recorded data may not be saved, and new data acquisition is desired at the third recording location.

At time t13, in response to the signal quality check changing from not satisfied to satisfied (plot 1004), the signal quality alert is turned off (plot 1008). At time t14, the first time duration d1 elapses with the signal quality check satisfied throughout the first time duration d1 (plot 1004). In response, the data recording at the third recording location is restarted (plot 1006).

At time t15, the second time duration d2 elapses with the signal quality check remaining satisfied throughout (plot 1004). Thus, the data recorded at the third recording location is of a high enough quality and quantity to be clinically relevant and may be saved to the electronic stethoscope and/or transmitted and saved to the computing device. With physiological data acquired at all of the prescribed recording locations, the exam is finished at time t15.

By guiding placement of the electronic stethoscope via augmented reality and performing the signal quality check in response to the visual placement being confirmed, a likelihood of the user placing the electronic stethoscope in such a way to obtain clinically relevant data at each recording location is increased. As a result of automatically recording the physiological data in response to the signal quality check being satisfied for the first time duration d1 and automatically stopping recording the physiological data in response to the signal quality check not being satisfied within the second time duration d2, a likelihood that clinically relevant data is acquired is increased, regardless of the user's technical skill, while an amount of manual input needed from the user is decreased.

Turning now to FIG. 11, a second example prophetic timeline 1100 for a medical examination having multiple prescribed recording locations for an electronic stethoscope is shown. Physiological data for the medical exam may be obtained by the electronic stethoscope operated in a second mode, such as the electronic stethoscope 100 shown in FIGS. 1A and 1B, in connection with a computing device, such as the external computing device 202 shown in FIG. 2. For example, the electronic stethoscope may wirelessly connect with the computing device, and the computing device may run a companion application to interface with the electronic stethoscope, such as described above with respect to FIGS. 4 and 6-9. In particular, the timeline 1100 provides an example of performing the medical examination without augmented reality guiding the placement of the electronic stethoscope, such as when a clinician conducts the medical exam on a patient. A signal quality check is shown in a plot 1102, a data recording plot is shown in a plot 1104, a signal quality alert is shown in a plot 1106, and a recoding location is shown in plot 1108.

For all of the above, the horizontal axis represents time, with time increasing along the horizontal axis from left to right. Vertical lines at times t0-t16 represent time points of interest. The plots shown in FIG. 11 are time aligned and occur at the same time. For plot 1102, the vertical axis indicates whether the signal quality check is satisfied or not satisfied, such as described above with respect to FIG. 10. For plot 1104, the vertical axis indicates whether the electronic stethoscope data recording is "on" or "off." For example, recorded physiological data may be saved to a memory of the electronic stethoscope and/or to a memory of the computing device. The electronic stethoscope may be continuously obtaining physiological data for the signal quality check, but the electronic stethoscope may not save that data. For plot 1106, the vertical axis indicates whether the signal quality alert is "on" or "off." For example, the signal alert may be on when the signal quality check is not satisfied. As another example, the signal quality alert may be off when the signal quality check is satisfied. For plot 1108, the vertical axis indicates the recording location of the electronic stethoscope. For example, the electronic stethoscope may be in a first recording location (e.g., "1'), a second recording location (e.g., "2"), or a third recording location (e.g., "3"). Although only three recording locations are shown in the example of timeline 1100, in other examples, there may be more or fewer locations without departing from the scope of this disclosure. Further, the first time duration d1 and the second time duration d2 introduced above with respect to FIG. 10 will be reference with respect to plot 1102.

At time to, the medical exam begins at the first recording location, as shown in plot 1108. From time t0 to time t1, the signal quality check (plot 1102) is not satisfied, which may be due to a user moving the electronic stethoscope into the correct position. As a result of the signal quality check not being satisfied, the signal quality alert (plot 1106) is on at time t0. However, at time t1, the signal quality check changes from not satisfied to satisfied. The first time duration d1 elapses at time t2, with the signal quality remaining satisfied throughout the first time duration d1. In response, data recording (plot 1104) is commenced at time t2. At time t3, the second time duration d2 elapses, with the recorded data signal quality check satisfied throughout the second time duration d2. As a result, the recorded data is acceptable for clinical use and may be saved to the electronic stethoscope and/or sent to the computing device.

With quality data obtained from the first recording location, the medical exam continues to the second recording location at time t3, as shown in plot 1108. From time t3 to time t4, the signal quality check (plot 1102) is not satisfied, and, because the signal quality check is not satisfied, the time duration d1 does not start. Additionally, because the signal quality check is not satisfied, the signal quality alert (plot 1106) is output beginning at time t3.

At time t4, the signal quality check is satisfied (plot 1102), and the signal quality alert is discontinued (plot 1106). However, the signal quality check does not remain satisfied for the first time duration d1, and so data recording remains off (plot 1104). Further, in response to the signal quality check no longer being satisfied at time t5, the signal quality alert is turned on (plot 1106) to alert the user to adjust the electronic stethoscope to increase the signal quality.

At time t6, the signal quality check changes from not satisfied to satisfied (plot 1102), and so the signal quality alert is turned off (plot 1106) while the first time duration d1 is restarted. At time t7, the first time duration d1 elapses, with the signal quality check remaining satisfied throughout. In response to the signal quality check remaining satisfied throughout the first time duration d1, the data recording (plot 1104) is turned on at time t7. At time t8, the second time duration d2 elapses. As a result of the signal quality check remaining satisfied (plot 1102) throughout the second time duration d2 between time t7 and time t8, the recorded data is acceptable for the medical exam and may be saved to the electronic stethoscope and/or sent to the computing device.

With the successful acquisition of physiological data from the second recording location of the medical exam, the medical exam changes to the third recording location at time t8, as shown by plot 1108. From time t8 to time t9, the signal quality check (plot 1102) is not satisfied, resulting in the signal quality alert (plot 1106) being output. The signal quality check may not be satisfied due to the electronic stethoscope position being adjusted from the second recording location to the third recording location, for example. At time t9, the signal quality check changes from not satisfied to satisfied (plot 1102).

At time t10, before the first time duration d1 fully elapses, the signal quality check changes from satisfied to not satisfied (plot 1102), resulting in the signal quality alert turning on (plot 1106). The signal quality alert is maintained on until time t11, at which time the signal quality check is satisfied (plot 1102). In response to the signal quality check being satisfied at time t11, the first time duration d1 is restarted.

At time t12, the first time duration d1 elapses with the signal quality check remaining satisfied (plot 1102). In response, the data recording (plot 1104) is commenced at time t12. However, at time t13, the signal quality check is no longer satisfied (plot 1102). As a result, the data recording turns off (plot 1104) and the signal quality alert turns on (plot 1106). Because the physiological data was not acquired for the second time duration d2, recording physiological data at the third location continues to be desired, and the partial data may not be stored.

At time t14, the signal quality check is again satisfied and remains satisfied for the first time duration d1, which elapses at time t15. As a result, the data recording is restarted at time t15. At time t16, the second time duration d2 elapses with the signal quality check remaining satisfied throughout (plot 1102), resulting in the recorded physiological data being acceptable for the medical exam. As a result, the physiological data for the third recording location may be saved to the electronic stethoscope and/or transmitted and saved to the computing device. With physiological data acquired at all of the prescribed recording locations, the exam is finished at time t16.

In this way, a workflow is provided that identifies accurate placement and/or high signal quality, resulting in a decreased examination time and decreased user effort. As a result, a medical exam may be accurately performed by a novice user, with or without real-time guidance from a clinician. By enabling the novice user to accurately gather clinically relevant physiological data, a utility of telehealth visits may be increased. Further, by automatically starting and stopping recording of the physiological data based on the signal quality of the physiological data, an examination burden is decreased on users of all skill levels, including clinicians. As a result, an amount of time spent performing the auscultation exam may be decreased.

The technical effect of automatically starting and stopping recording of physiological data by an electronic stethoscope based on a signal quality of the physiological data is that a clinical relevance of the recorded physiological data is increased while user time and effort is decreased.

The disclosure also provides support for a method, comprising: performing a signal quality check of an electronic stethoscope at a first recording location on a subject, recording physiological data for an exam at the first recording location via the electronic stethoscope in response to the signal quality check satisfying a quality threshold, and outputting a signal quality alert in response to the signal quality check not satisfying the quality threshold. In a first example of the method, the physiological data include one or both of audio data and electrocardiogram (ECG) data. In a second example of the method, optionally including the first example, performing the signal quality check includes analyzing a smaller amount of the physiological data than is recorded for the exam. In a third example of the method, optionally including one or both of the first and second examples, the signal quality check uses a machine learning algorithm to extract data patterns of the physiological data and compare the extracted data patterns to a model that is specific to a current recording location. In a fourth example of the method, optionally including one or more or each of the first through third examples, the exam is an auscultation exam having multiple prescribed recording locations, and the method further comprises: outputting an alert to position the electronic stethoscope at a second recording location on the subject after recording the physiological data at the first recording location, performing the signal quality check of the electronic stethoscope at the second recording location on the subject, recording the physiological data for the exam at the second recording location via the electronic stethoscope in response to the signal quality check satisfying the quality threshold, and outputting the signal quality alert in response to the signal quality check at the second recording location not satisfying the quality threshold. In a fifth example of the method, optionally including one or more or each of the first through fourth examples, the signal quality alert includes one or more of an audible alert, a visual alert, and haptic feedback. In a sixth example of the method, optionally including one or more or each of the first through fifth examples, the electronic stethoscope is wirelessly connected to a computing device, and wherein the signal quality alert is output on one or both of the electronic stethoscope and the computing device. In a seventh example of the method, optionally including one or more or each of the first through sixth examples, the method further comprises: displaying, on a display of a computing device communicatively coupled to the electronic stethoscope, a desired position of the electronic stethoscope at the first recording location on the subject, and wherein performing the signal quality check of the electronic stethoscope is responsive to obtaining a visual confirmation of a placement of the electronic stethoscope at the first recording location. In an eighth example of the method, optionally including one or more or each of the first through seventh examples, obtaining the visual confirmation of the placement of the electronic stethoscope at the first recording location comprises: obtaining live images of the subject and the electronic stethoscope via a camera of the computing device, comparing a current position of the electronic stethoscope in the live images with the desired position of the electronic stethoscope at the first recording location, confirming the placement of the electronic stethoscope at the first recording location on the subject in response to a distance between the current position of the electronic stethoscope and the desired position being less than a threshold distance, and not confirming the placement of the electronic stethoscope at the first recording location on the subject in response to the distance between the current position of the electronic stethoscope and the desired position being greater than the threshold distance. In a ninth example of the method, optionally including one or more or each of the first through eighth examples, the method further comprises: outputting an adjustment alert in response to the distance between the current position of the electronic stethoscope and the desired position being greater than the threshold distance.

The disclosure also provides support for a method for a medical exam using an electronic stethoscope, comprising: while operating the electronic stethoscope in a first mode, visually guiding a placement of the electronic stethoscope via augmented reality prior to performing a signal quality check of the electronic stethoscope. In a first example of the method, visually guiding the placement of the electronic stethoscope via the augmented reality comprises: connecting the electronic stethoscope to an external computing device, obtaining real-time images of a patient and the electronic stethoscope via a camera of the external computing device, displaying, on a display of the external computing device, the real-time images of the patient and the electronic stethoscope, determining a desired recording location on the patient based on settings of the medical exam and an analysis of the patient from the real-time images, and displaying, on the real-time images of the patient and the electronic stethoscope, a placement indicator for the electronic stethoscope at the desired recording location on the patient. In a second example of the method, optionally including the first example, visually guiding the placement of the electronic stethoscope via the augmented reality further comprises: determining a percentage overlap between a current position of the electronic stethoscope in the real-time images and the placement indicator, confirming the placement of the electronic stethoscope at the desired recording location on the patient in response the percentage overlap being greater than or equal to a threshold, and not confirming the placement of the electronic stethoscope at the desired recording location on the patient in response to the percentage overlap between the current position of the electronic stethoscope and the placement indicator being less than the threshold. In a third example of the method, optionally including one or both of the first and second examples, performing the signal quality check of the electronic stethoscope is responsive to confirming the placement of the electronic stethoscope. In a fourth example of the method, optionally including one or more or each of the first through third examples, the method further comprises: while operating the electronic stethoscope in a second mode, performing the signal quality check without visually guiding the placement of the electronic stethoscope. In a fifth example of the method, optionally including one or more or each of the first through fourth examples, performing the signal quality check comprises sampling physiological data via the electronic stethoscope and inputting the sampled physiological data into a machine learning algorithm that determines whether the signal quality check is satisfied, and wherein the method further comprises automatically recording the physiological data for the medical exam via the electronic stethoscope in response to the signal quality check being satisfied.

The disclosure also provides support for a system for performing an auscultation exam, comprising: an electronic stethoscope, and a processor operatively coupled to a memory storing instructions that, when executed by the processor, cause the processor to: evaluate a quality of a signal recorded by the electronic stethoscope based on a recording location of the electronic stethoscope, wirelessly transmit the recorded signal to an external computing device in response to the quality of the signal being greater than a threshold, and discontinue transmission of the recorded signal in response to the quality of the signal decreasing below a threshold. In a first example of the system, to evaluate the quality of the signal recorded by the electronic stethoscope based on the recording location of the electronic stethoscope, the memory stores further instructions that, when executed by the processor, cause the processor to: select a model specific to the recording location from a plurality of models for a plurality of recording locations, and evaluate the quality of the signal recorded by the electronic stethoscope using only the selected model via a machine learning algorithm. In a second example of the system, optionally including the first example, each model of the plurality of models is trained using both high quality data that is greater than the threshold and low quality data that is not greater than the threshold for a corresponding recording location. In a third example of the system, optionally including one or both of the first and second examples, the memory stores further instructions that, when executed by the processor, cause the processor to: visually confirm placement of the electronic stethoscope at the recording location via live images obtained by the external computing device prior to evaluating the quality of the signal recorded by the electronic stethoscope.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:

performing a signal quality check of an initial sample of physiological data from an electronic stethoscope at a first recording location on a subject, the signal quality check including selecting a model specific to the first recording location from a plurality of models for a plurality of recording locations and evaluating a quality of the initial sample using only the selected model via a machine learning algorithm;

recording further physiological data for an exam at the first recording location via the electronic stethoscope in response to the signal quality check satisfying a quality threshold; and outputting a signal quality alert in response to the signal quality check not satisfying the quality threshold.

2. The method of claim 1, wherein the initial sample of physiological data and further physiological data include one or both of audio data and electrocardiogram (ECG) data.

3. The method of claim 1, wherein the initial sample of physiological data used for performing the signal quality check includes a smaller amount of physiological data than is recorded for the exam.

4. The method of claim 1, wherein the exam is an auscultation exam having multiple prescribed recording locations, and the method further comprises:

outputting an alert to position the electronic stethoscope at a second recording location on the subject after recording the further physiological data at the first recording location;

performing a second signal quality check of the electronic stethoscope at the second recording location on the subject;

recording additional physiological data for the exam at the second recording location via the electronic stethoscope in response to the second signal quality check satisfying the quality threshold; and outputting the signal quality alert in response to the second signal quality check at the second recording location not satisfying the quality threshold.

5. The method of claim 1, wherein the signal quality alert includes one or more of an audible alert, a visual alert, and haptic feedback.

6. The method of claim 1, wherein the electronic stethoscope is wirelessly connected to a computing device, and wherein the signal quality alert is outputted on one or both of the electronic stethoscope and the computing device.

7. The method of claim 1, further comprising displaying, on a display of a computing device communicatively coupled to the electronic stethoscope, a desired position of the electronic stethoscope at the first recording location on the subject, and wherein performing the signal quality check of the electronic stethoscope is responsive to obtaining a visual confirmation of a placement of the electronic stethoscope at the first recording location.

8. The method of claim 7, wherein obtaining the visual confirmation of the placement of the electronic stethoscope at the first recording location comprises:

obtaining live images of the subject and the electronic stethoscope via a camera of the computing device;

comparing a current position of the electronic stethoscope in the live images with the desired position of the electronic stethoscope at the first recording location;

confirming the placement of the electronic stethoscope at the first recording location on the subject in response to a distance between the current position of the electronic stethoscope and the desired position being less than a threshold distance; and not confirming the placement of the electronic stethoscope at the first recording location on the subject in response to the distance between the current position of the electronic stethoscope and the desired position being greater than the threshold distance.

9. The method of claim 8, further comprising outputting an adjustment alert in response to the distance between the current position of the electronic stethoscope and the desired position being greater than the threshold distance.

10. A method for a medical exam using an electronic stethoscope, comprising:

while operating the electronic stethoscope in a first mode, visually guiding a placement of the electronic stethoscope via augmented reality prior to performing a signal quality check of the electronic stethoscope; and responsive to confirming the placement of the electronic stethoscope at a desired recording location, performing the signal quality check, including selecting a model specific to the desired recording location from a plurality of models for a plurality of recording locations and evaluating a quality of a signal recorded by the electronic stethoscope using only the selected model via a machine learning algorithm.

11. The method of claim 10, wherein visually guiding the placement of the electronic stethoscope via the augmented reality comprises:

connecting the electronic stethoscope to an external computing device;

obtaining real-time images of a patient and the electronic stethoscope via a camera of the external computing device;

displaying, on a display of the external computing device, the real-time images of the patient and the electronic stethoscope;

determining a desired recording location on the patient based on settings of the medical exam and an analysis of the patient from the real-time images; and displaying, on the real-time images of the patient and the electronic stethoscope, a placement indicator for the electronic stethoscope at the desired recording location on the patient.

12. The method of claim 11, wherein visually guiding the placement of the electronic stethoscope via the augmented reality further comprises:

determining a percentage overlap between a current position of the electronic stethoscope in the real-time images and the placement indicator;

confirming the placement of the electronic stethoscope at the desired recording location on the patient in response the percentage overlap being greater than or equal to a threshold; and not confirming the placement of the electronic stethoscope at the desired recording location on the patient in response to the percentage overlap between the current position of the electronic stethoscope and the placement indicator being less than the threshold.

13. The method of claim 10, wherein the method further comprises automatically recording physiological data for the medical exam via the electronic stethoscope in response to the signal quality check being satisfied.

14. A system for performing an auscultation exam, comprising:

an electronic stethoscope; and a processor operatively coupled to a memory storing instructions that, when executed by the processor, cause the processor to:

evaluate a quality of a signal recorded by the electronic stethoscope based on a recording location of the electronic stethoscope;

wirelessly transmit the recorded signal to an external computing device in response to the quality of the signal being greater than a threshold; and discontinue transmission of the recorded signal in response to the quality of the signal decreasing below the threshold, wherein to evaluate the quality of the signal recorded by the electronic stethoscope based on the recording location of the electronic stethoscope, the memory stores further instructions that, when executed by the processor, cause the processor to:

select a model specific to the recording location from a plurality of models for a plurality of recording locations; and evaluate the quality of the signal recorded by the electronic stethoscope using only the selected model via a machine learning algorithm.

15. The system of claim 14, wherein each model of the plurality of models is trained using both high quality data that is greater than the threshold and low quality data that is not greater than the threshold for a corresponding recording location.

16. The system of claim 14, wherein the memory stores further instructions that, when executed by the processor, cause the processor to:

visually confirm placement of the electronic stethoscope at the recording location via live images obtained by the external computing device prior to evaluating the quality of the signal recorded by the electronic stethoscope.

* * * * *